(12) United States Patent
Herwig et al.

(10) Patent No.: US 11,078,898 B2
(45) Date of Patent: Aug. 3, 2021

(54) PORTABLE DEVICE WITH DISPOSABLE RESERVOIR FOR COLLECTION OF INTERNAL FLUID AFTER SURGERY

(71) Applicants: Joshua D. Herwig, Memphis, TN (US); Esra Roan, Memphis, TN (US); Nathaniel F. Stoikes, Memphis, TN (US); Guy Voeller, Germantown, TN (US)

(72) Inventors: Joshua D. Herwig, Memphis, TN (US); Esra Roan, Memphis, TN (US); Nathaniel F. Stoikes, Memphis, TN (US); Guy Voeller, Germantown, TN (US)

(73) Assignee: SOMAVAC MEDICAL SOLUTIONS, INC., Memphis, TN (US)

( * ) Notice: Subject to any disclaimer, the term of this patent is extended or adjusted under 35 U.S.C. 154(b) by 789 days.

(21) Appl. No.: 15/604,254

(22) Filed: May 24, 2017

(65) Prior Publication Data
US 2018/0001000 A1 Jan. 4, 2018

Related U.S. Application Data

(60) Provisional application No. 62/409,400, filed on Oct. 18, 2016, provisional application No. 62/340,853, filed on May 24, 2016.

(51) Int. Cl.
*A61M 39/00* (2006.01)
*F04B 43/14* (2006.01)
(Continued)

(52) U.S. Cl.
CPC .......... *F04B 43/14* (2013.01); *A61M 1/0023* (2013.01); *A61M 1/0231* (2014.02); *A61M 1/631* (2021.05); *A61M 1/73* (2021.05); *A61M 1/88* (2021.05); *A61M 1/90* (2021.05); *A61M 1/962* (2021.05); *A61M 39/00* (2013.01); *F04B 43/04* (2013.01); *A61M 2205/14* (2013.01);
(Continued)

(58) Field of Classification Search
CPC .............. A61M 1/0001; A61M 1/0019; A61M 1/0023; A61M 1/0007; A61M 1/0025; A61M 1/009; A61M 1/0094; A61M 1/0231; A61M 1/0088; A61M 2209/088
See application file for complete search history.

(56) References Cited

U.S. PATENT DOCUMENTS

| | | | | |
|---|---|---|---|---|
| 4,909,713 A | * | 3/1990 | Finsterwald | ........ F04B 43/1253 417/477.1 |
| 4,930,997 A | * | 6/1990 | Bennett | ............... A61M 1/0019 417/410.1 |

(Continued)

*Primary Examiner* — Ariana Zimbouski
(74) *Attorney, Agent, or Firm* — William S. Parks; Susan A. Sentress

(57) ABSTRACT

A system and apparatus for the collection of serous or serosanguinous fluid from a percutaneous site after surgery. A pump unit with one or more pumps or powered sources provide continuous negative pressure suction to draw fluid from the percutaneous site and pumps the fluid into disposable reservoirs with one-way valves that are easy to handle while maintaining sterility and a seal to prevent the loss of vacuum. Air is continuously removed from the reservoirs. Measurement and analysis of the output is performed automatically.

17 Claims, 26 Drawing Sheets

(51) Int. Cl.
    *A61M 1/00*     (2006.01)
    *A61M 1/02*     (2006.01)
    *F04B 43/04*     (2006.01)

(52) U.S. Cl.
    CPC ........... *A61M 2205/3324* (2013.01); *A61M 2205/3389* (2013.01); *A61M 2205/3576* (2013.01); *A61M 2209/088* (2013.01)

(56) References Cited

U.S. PATENT DOCUMENTS

| | | | | |
|---|---|---|---|---|
| 5,549,584 A * | 8/1996 | Gross | | A61M 1/0088 604/313 |
| 6,142,982 A * | 11/2000 | Hunt | | A61M 1/0023 604/313 |
| 2007/0055209 A1* | 3/2007 | Patel | | A61M 1/0088 604/315 |
| 2007/0293830 A1* | 12/2007 | Martin | | A61M 3/0216 604/289 |
| 2009/0306610 A1* | 12/2009 | Van Den Heuvel | | A61F 5/451 604/317 |
| 2010/0179493 A1* | 7/2010 | Heagle | | A61M 1/784 604/313 |
| 2011/0060300 A1* | 3/2011 | Weig | | A61M 1/743 604/319 |
| 2011/0130712 A1* | 6/2011 | Topaz | | A61M 1/0031 604/23 |
| 2012/0029448 A1* | 2/2012 | Ehlert | | A61M 1/0001 604/319 |
| 2012/0248017 A1* | 10/2012 | Beiriger | | A61M 1/1605 210/143 |
| 2013/0226114 A1* | 8/2013 | Massi | | A61M 1/0023 604/318 |
| 2014/0228784 A1* | 8/2014 | Mazzoni | | A61M 1/0088 604/305 |
| 2015/0246164 A1* | 9/2015 | Heaton | | A61M 1/0088 604/313 |

\* cited by examiner

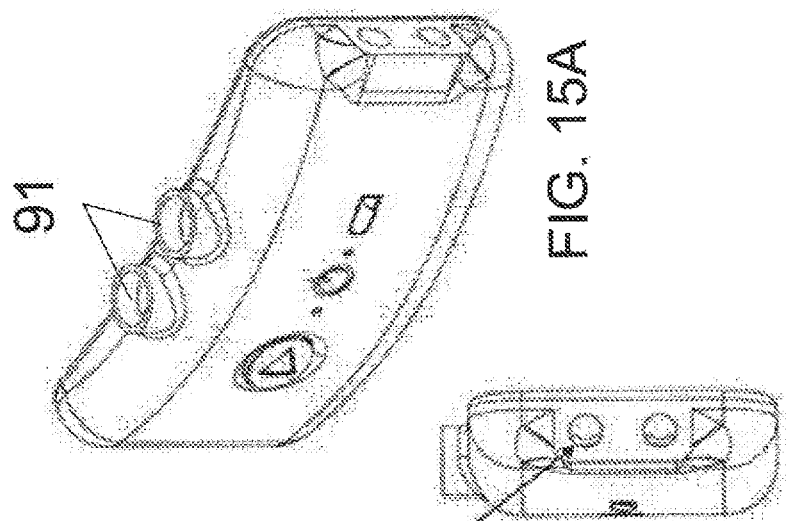
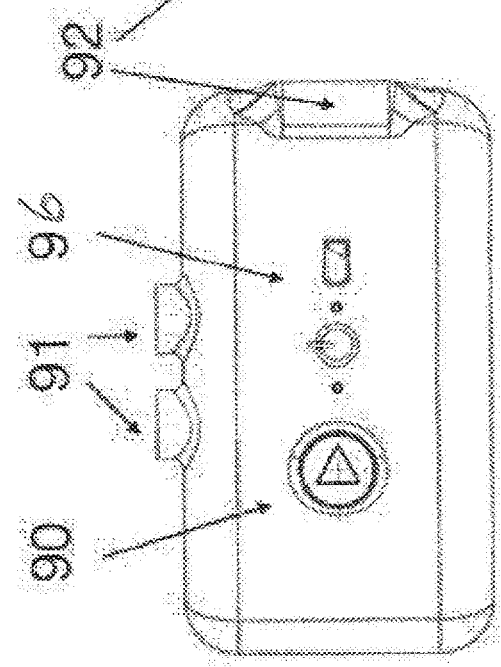
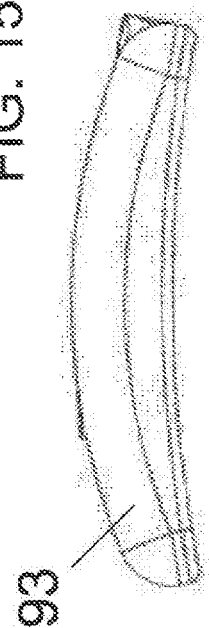
FIG. 15A
FIG. 15B
FIG. 15C

PORTABLE DEVICE WITH DISPOSABLE RESERVOIR FOR COLLECTION OF INTERNAL FLUID AFTER SURGERY

This application claims benefit of and priority to U.S. Provisional Applications Nos. 62/340,853, filed May 24, 2016, and 62/409,400, filed Oct. 18, 2016, and is entitled to priority to those filing dates. The specifications, drawings, appendices, and complete disclosures of U.S. Provisional Applications Nos. 62/340,853 and 62/409,400 are incorporated herein by specific reference for all purposes.

FIELD OF INVENTION

This invention relates to medical devices, particularly those used to drain serous or serosanguinous fluid from the percutaneous site after surgery.

BACKGROUND OF THE INVENTION

In order to drain the fluid which naturally builds up after surgeries such as mastectomies, abdominoplasties, panniculectomies, hernia repair, and the like, surgeons place drains attached to reservoirs which collect the bodily fluids for a period of time ranging from several days to several months. Once the bulbs are filled, the patient or an aide empties the contents into a measuring cup, measures and reports the amounts of collected fluid to the healthcare provider. The daily collected amount is the determinant of the clinical decision, i.e., the removal of the drains. Patients strongly dislike the drains due to quality of life issues, but yet it is their self-reported values that determine the clinical course. This conflict of interest jeopardizes the optimal care of the patient.

Despite prior attempts to reduce the risk of postoperative seromas due to large flap forming surgeries, no single technique has been shown to eliminate the risk completely. Current solutions are passive, tend to clog, are ineffective in removing fluid, are much disliked by patients and healthcare providers, and lack any diagnostic capability.

One of the major issues with post-surgical fluid management is the storage of the collected fluids. There are large amounts of fluid that is collected in patients who undergo large void-forming surgeries. This results in large volumes to be collected, measured, and emptied. The patients wear graduated bulbs in which fluid is collected and measured by patients themselves. Multiple issues relate to this: (1) fluid is collected only after all the air is removed from the abdomen; (2) patients have to pour the fluid in a measuring cup, measure, record, and report to their healthcare provider, (3) maintenance of sterility is difficult. In order to effectively remove the fluid in a continuous manner, air must be removed from the collection reservoir. Otherwise, either the reservoir is filled quickly with air/liquid mixture and emptying must take place to remove fluid often, or the reservoir overfills leading to high pressure levels and possibly backflow.

Devices which are designed to remove serous or serosanguinous fluid from the internal percutaneous space of a patient after surgery are cumbersome for patients to manage, and apply severely limited pressure to the internal space resulting in ineffective drainage and the development of blockages in the drainage lines.

Accordingly, there is a need for a device that that addresses these problems and issues with a comprehensive approach.

SUMMARY OF INVENTION

In various exemplary embodiments, the present invention comprises a system and apparatus for the collection of serous or serosanguinous fluid from the percutaneous site after surgery. There are large amounts of fluid that collect in patients who undergo large void-forming surgeries. This results in large volumes to be collected, measured, and emptied. In order to effectively remove the fluid in a continuous manner, air must be removed from the collection reservoir. Otherwise, either the reservoir is filled quickly with air/liquid mixture and emptying must take place to remove fluid often, or the reservoir overfills leading to high pressure levels and possibly backflow.

In several embodiments, the present invention makes use of a powered source of negative pressure which helps overcome clogging observed in prior art devices, and one or more reservoirs which allow excess air to be removed. The invention comprises disposable reservoirs with one-way valves that are easy to handle while maintaining sterility and a seal to prevent the loss of vacuum. The present invention further provides continuous negative pressure suction which assists in providing constant drainage. Prior art devices do not provide a means of applying continuous negative pressure to the percutaneous wound site.

In addition, the measurements of the output can be performed automatically, relieving the need for the patient to perform measurements directly (and thus resolving the potential conflict of interest in self-measuring so that the best clinical decisions can be made). The measurements of output can be relayed to the caregiver, doctor, or the nurse via wired or wireless communications, and enables patients who do not have companions to manage their drain care. There is a potential diagnostic value in taking various measurements associated with the collected fluid. Measurements can include and are not limited to collected fluid amount, pH, certain known harmful mediators (cytokines, chemokines, reactive oxygen species), protein levels, blood content, etc. For example, amount of fluid collected can be an indicator of possible seroma development in some hernia surgeries. Additionally, pH has also been shown to act as an indicator of possible seroma formation. The present invention thus allows for the detection of infectious materials, and any other chemicals or substances which may indicate infection, or the presence of some medical condition which may naturally arise in response to the surgical procedure, initial pathology, or additional complications (of either the surgical procedure or the initial pathology) in the fluid collected from percutaneous (internal) wounds.

BRIEF DESCRIPTION OF THE DRAWINGS

FIG. 15A is a perspective view of the pump housing of FIG. 14.

FIG. 15B shows front and end views of the pump housing of FIG. 15A.

FIG. 15C shows a bottom view of the pump housing of FIG. 15A.

DETAILED DESCRIPTION OF EXEMPLARY EMBODIMENTS

In various exemplary embodiments, the present invention comprises a system and apparatus for the collection of serous or serosanguinous fluid from the percutaneous site after surgery. There are large amounts of fluid that collect in patients who undergo large void-forming surgeries. This results in large volumes to be collected, measured, and emptied. In order to effectively remove the fluid in a continuous manner, air must be removed from the collection reservoir. Otherwise, either the reservoir is filled quickly with air/liquid mixture and emptying must take place to remove fluid often, or the reservoir overfills leading to high pressure levels and possibly backflow.

In several embodiments, the present invention makes use of a powered source of negative pressure which helps overcome clogging observed in prior art devices, and one or more reservoirs which allow excess air to be removed. The invention comprises disposable reservoirs with one-way valves that are easy to handle while maintaining sterility and a seal to prevent the loss of vacuum. The present invention further provides continuous negative pressure suction which assists in providing constant drainage. Prior art devices do not provide a means of applying continuous negative pressure to the percutaneous wound site.

In addition, the measurements of the output can be performed automatically, relieving the need for the patient to perform measurements directly (and thus resolving the potential conflict of interest in self-measuring so that the best clinical decisions can be made). The measurements of output can be relayed to the caregiver, doctor, or the nurse via wired or wireless communications, and enables patients who do not have companions to manage their drain care. There is a potential diagnostic value in taking various measurements associated with the collected fluid. Measurements can include and are not limited to collected fluid amount, pH, certain known harmful mediators (cytokines, chemokines, reactive oxygen species), protein levels, blood content, etc. For example, amount of fluid collected can be an indicator of possible seroma development in some hernia surgeries. Additionally, pH has also been shown to act as an indicator of possible seroma formation. The present invention thus allows for the detection of infectious materials, and any other chemicals or substances which may indicate infection, or the presence of some medical condition which may naturally arise in response to the surgical procedure, initial pathology, or additional complications (of either the surgical procedure or the initial pathology) in the fluid collected from percutaneous (internal) wounds.

Figure 1:
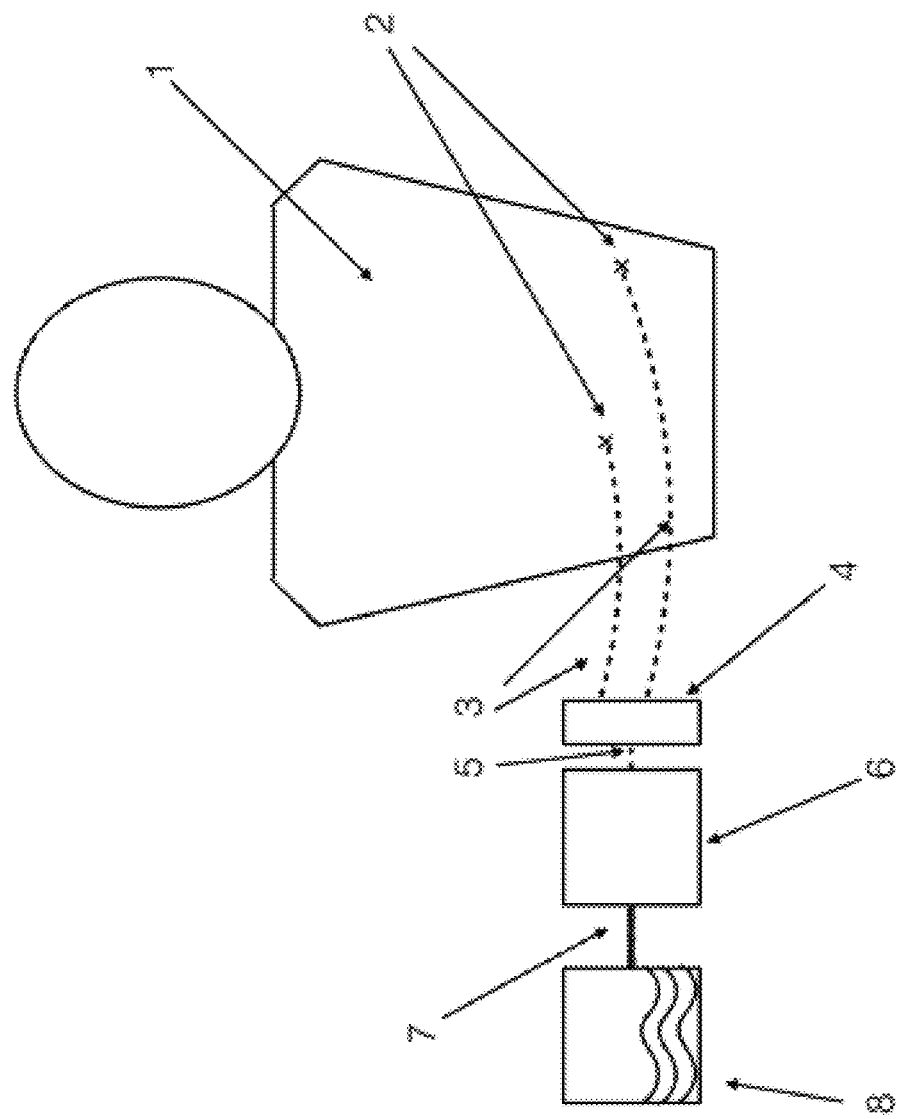
FIG. 1 is a perspective view of an exemplary embodiment of the device and patient.

FIG. 1 shows an exemplary embodiment of the present system. Drainage structures 3 begin in the percutaneous space, extend through the percutaneous tissue at an exit site 2 and terminate in the multiple-drainage-structure manifold 4. A pump 6 creates a negative pressure in the connection 5 between the pump 6 and manifold 4 and imparts a negative pressure to the single or multiple drainage structures 3. The pump 6, by employing either a peristaltic mechanism, positive displacement, or some other source conveys positive pressure to the collected fluid after it enters the pump unit, which causes the fluid to be transported to the disposable reservoir 8. A series of one way valves which may be placed at either one or all of the following locations ensure the prevention of backflow: at the manifold entrance, pump entrance and exit, and reservoir entrance.

The pump 6 is controlled by means of an onboard processor which may take as inputs from the user the following: on/off; desired pump pressure; and device communication parameters (i.e., mobile device connectivity and the selection of default mobile device). Additionally, the onboard processor may take as inputs from the device the following: pump pressure differential (between exit 2 and pump entrance); flow rate at manifold (for each individual drainage structure or for all drainage structures combined); motor current draw; device orientation with respect to force of gravity (from accelerometer); presence of bacterial or pathogenic substances; immune system indicators; battery charge level; or any value relevant to the operation of the device.

The device may communicate via Bluetooth or some other communication protocol (e.g., BLE, NFC) to a mobile device or to a larger cellular network in order to provide information regarding the performance of the device (e.g., battery charge level, need to change reservoir, device temperature, current magnitude of negative pressure, presence of blockage in tubing, or any other relevant information which may be of benefit to either the patient, their nurse, their doctor, their caregivers, their family, or any interested party) and the characteristics of the collected fluids. These characteristics may include, but are not limited to, the following: total collected amount (either total or per drainage structure); rate of fluid collection (total or per drainage structure) over one or more time scales (e.g., hours, days, or weeks); presence of infectious materials; and the presence of any other chemicals or substances which may indicate infection or the presence of some medical condition which may naturally arise in response to the surgical procedure, initial pathology, or additional complications (of either the surgical procedure or the initial pathology) in the fluid collected from percutaneous (internal) wounds. This information may be relayed to a mobile computing device, personal computer, or any computer or database system which may be accessed by the staff of an inpatient or outpatient medical center, the patient, their nurse, their doctor, their caregivers, their family, or any interested party as allowed by law. This information may be accessed by a purposefully designed mobile application on the mobile computing devices of the patient, their nurse, their doctor, their caregivers, their family, or any interested party as allowed by law.

Figure 2:
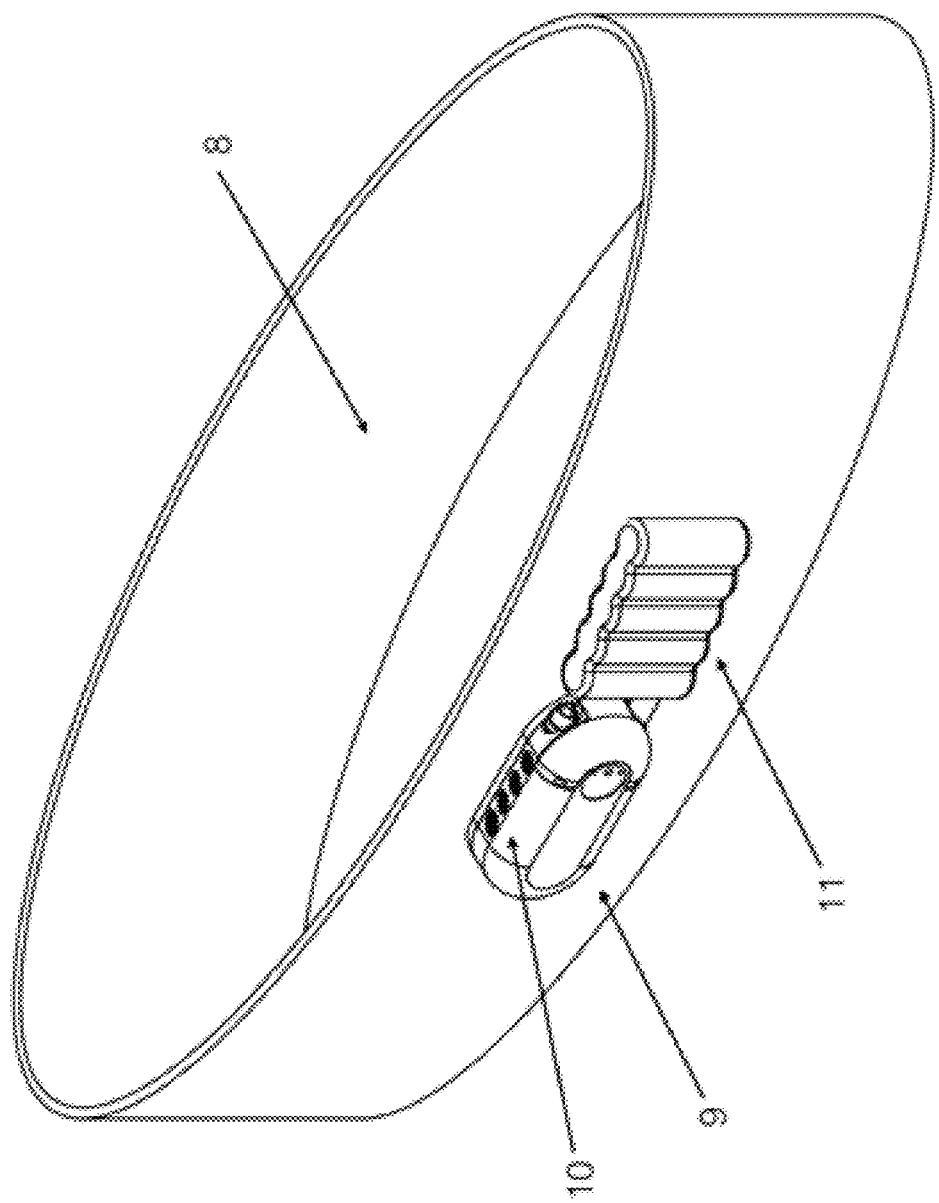
FIG. 2 is a perspective view of one embodiment of the device incorporated into an abdominal binder.

FIG. 2 shows a perspective view of a pump 9, manifold 10, and disposable reservoir 11 placed onto an abdominal binder 8. This arrangement comprises a single unit generally placed at the end of the surgical procedure. The device components may connect to the binder by means of a removable fastening system so that it may be removed from the binder to facilitate patient comfort. Additionally, the binder may incorporate some means to secure the drainage structure (drainage tubing) at the surgical exit site, and along its path to the pump unit. Furthermore the binder may fasten to itself (forming a continuous loop) by means of hook-and-loop fabric connection, buckle connector, or button snap connector(s). The location at which the pump unit attaches to the abdominal binder may incorporate some means of heat mitigation, such as, but not limited to, an open-cell foam pad, or gel-filled plastic pouch type pad.

Figure 3:
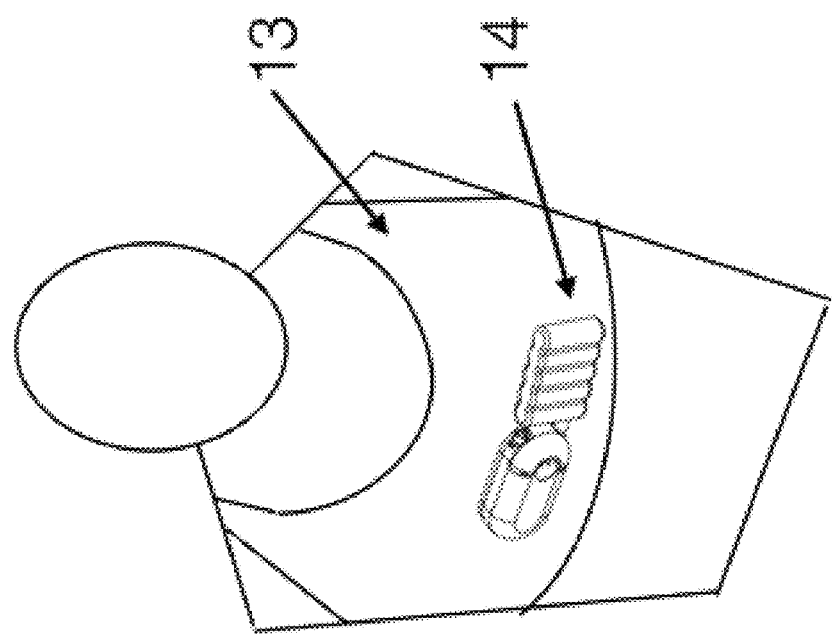
FIG. 3 is a perspective view of one embodiment of the device incorporated into a bra for use after mastectomy.

In an alternative embodiment, FIG. 3 shows a perspective view of a combined pump, manifold, and disposable reservoir unit 14 placed on a bra 13 or mastectomy binder, which is commonly used following a mastectomy procedure. This allows a single unit which is generally to be placed at the end of the surgical procedure. The device 14 may connect or be attached to the bra 13 by means of a removable fastener (as described above) so that it may be removed from the binder to facilitate patient comfort. Additionally, the bra may incorporate some means to secure the drainage structure (drainage tubing) at the surgical exit site, and along its path to the pump unit.

Figure 4B:
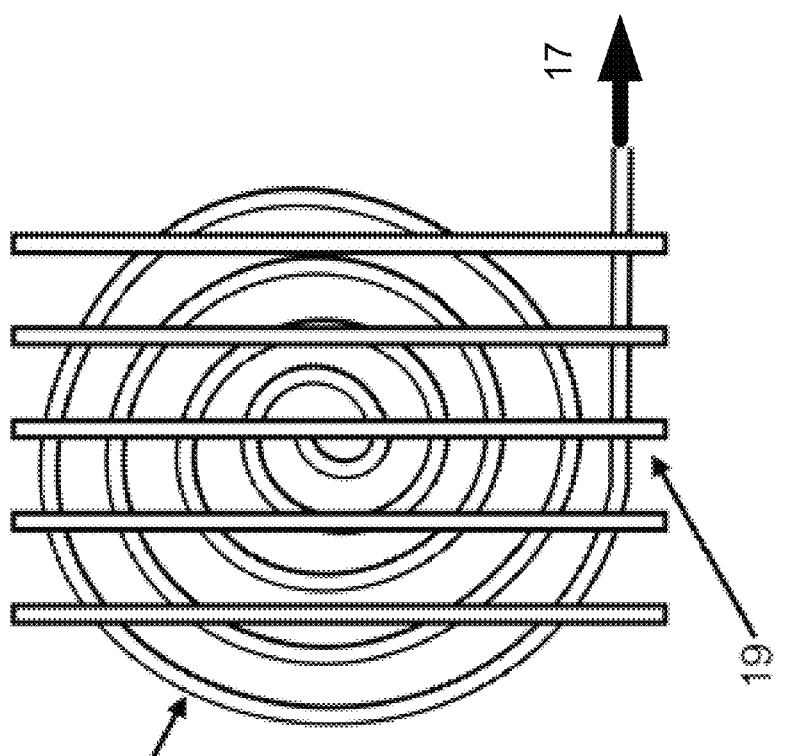
FIGS. 4A-B are views of exemplary embodiments of drainage structures which may be connected to the source of negative pressure.
Figure 4A:
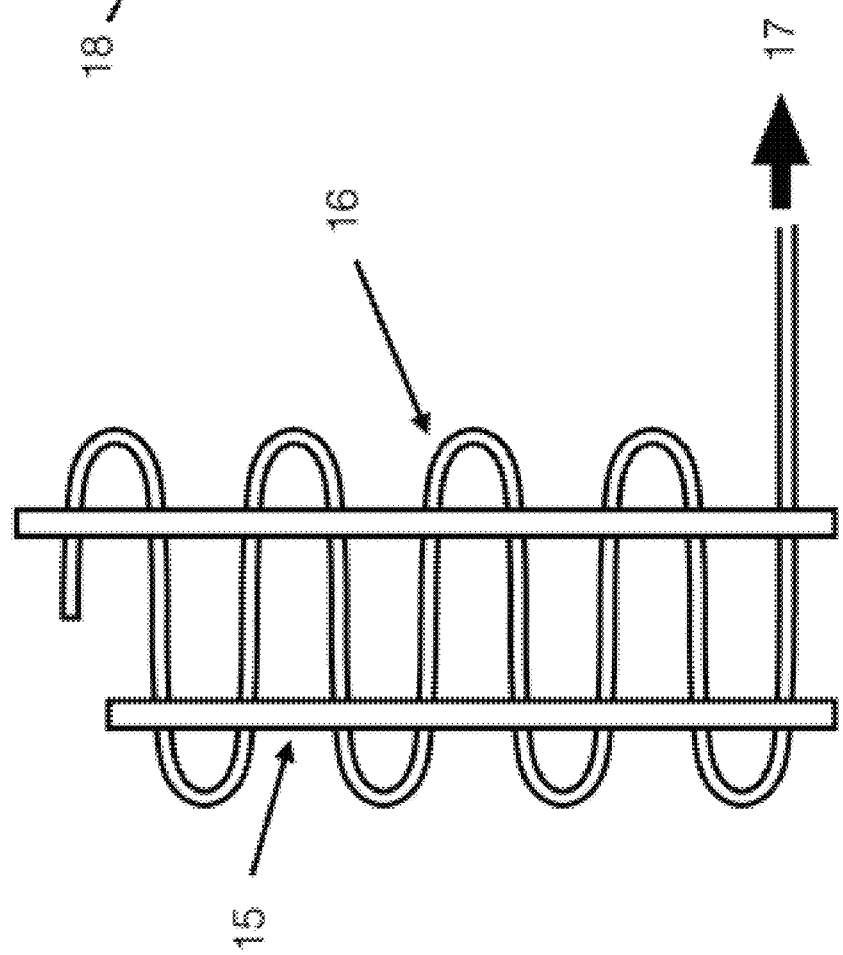

FIGS. 4A-B shows views of possible internal drainage structures placed inside of the percutaneous space at the time of surgery. A hollow flexible tube 16, 18 may be perforated, or may incorporate some cross section which facilitates the drainage of fluid and prevents tissue ingrowth into the tubing. Scaffolding 15, 19 holds the drainage structure in the conformation which increases surface area. The scaffolding units may be biodegradable or resorbable, and may incorporate different geometry, number, or conformation than shown in the figures. Additionally, these scaffolding units may incorporate antibacterial substances, or any substance which may aid in the tissue apposition of the wound space, healing, infection prevention, blood clot formation, or any other medically useful property. The scaffolding may adhere to the surface of the drainage tubing, or may incorporate such geometry as is necessary to allow the scaffolding to completely encapsulate the drainage tubing at the points of intersection. The drainage structure continues 17 through the percutaneous tissue through the exit site and terminates at the fluid collection unit or drainage bulb. While the drainage structures shown in FIGS. 4A-B are embodiments of the unique drainage structure, many other possible configurations are possible which utilize resorbable or biodegradable scaffolds to form the geometry of the drainage suture.

Figure 5:
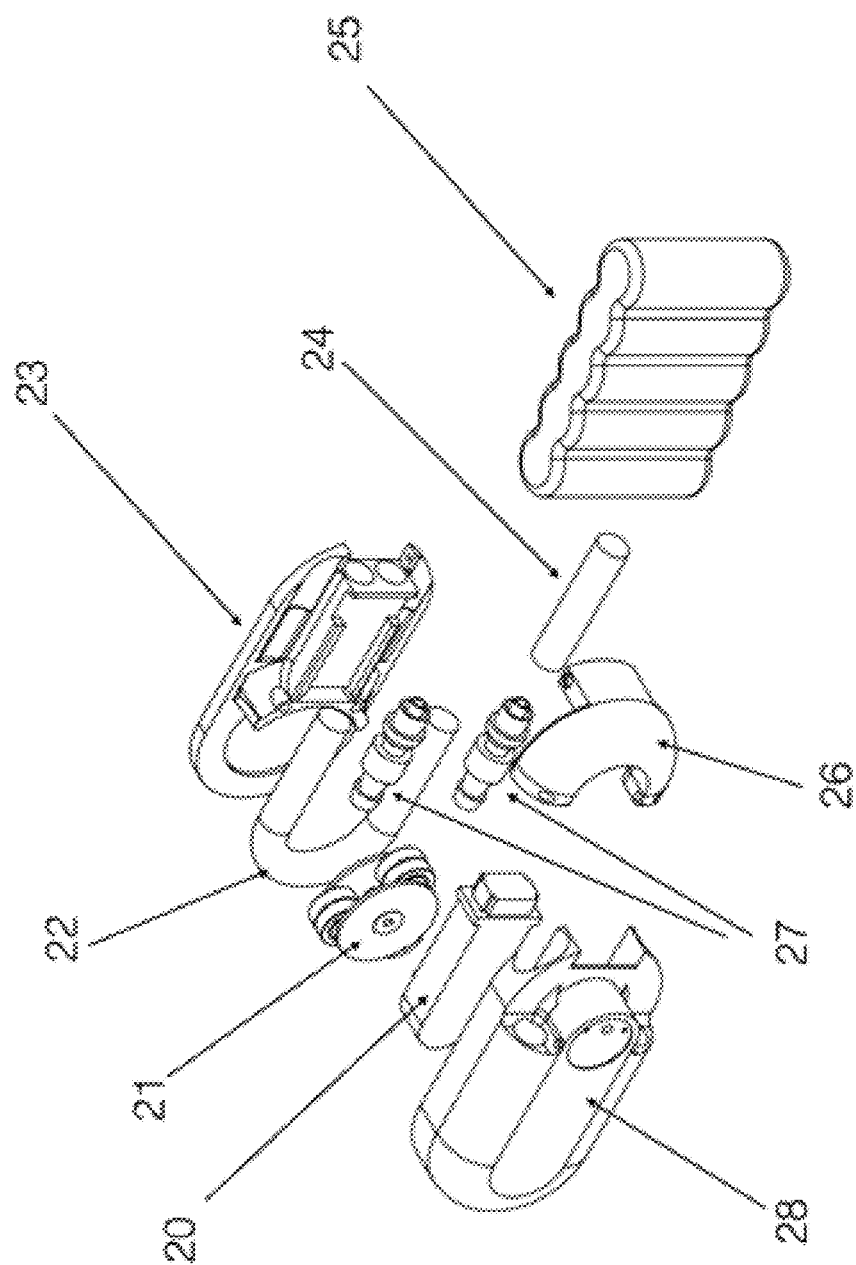
FIG. 5 is a perspective view of one embodiment of the pump device.

FIG. 5 shows a perspective view of one embodiment of the pump mechanism. The top housing (front 28 and rear 23) provides the main structural support for the device, and may also provide the contact path necessary for the peristaltic action or positive displacement to occur. Furthermore, it may house all necessary electronic components which include, but are not limited to, the microprocessor/microcontroller, the battery charging components, the user interface components (buttons, switches, displays), the communication components and circuitry, and all necessary wiring and small components. The peristaltic action is accomplished by the central rolling mechanism 21 sequentially compressing the internal tubing 22 which may consist of silicone rubber or any similar flexible material which may have desirable properties for this application. The driving force needed to rotate the central rolling mechanism is provided by an electric motor 20 which may be powered by either a rechargeable or a non-rechargeable battery source. In one embodiment, the motor is a 6V DC motor with a 90 degree output shaft in order to reduce the overall device profile. The majority of the electrical components are contained within the rear device housing 23. This also provides some storage space for batteries.

Sterile, one-way valves 27 prevent backflow of the fluid at both the pump entrance, and also at the pump exit (reservoir entrance). Fluid is transferred from the pump to the reservoir 25 through either direct connection or via additional tubing 24 to allow the reservoir to be placed at a distance away from the pump. The reservoir may be either soft flexible plastic or a hard, rigid container, or a combination of both in which a flexible plastic pouch is placed within a rigid outer container. As the reservoir 24 is placed downstream from the pump unit, it must provide for the release of excess air which may otherwise become trapped in the reservoir. Air-permeable, liquid-impermeable membranes may be incorporated into the reservoir in order to allow this air to escape. Furthermore the entire reservoir may be comprised of an air-permeable, liquid-impermeable material.

The pump unit may have features which allows it to be easily attached to an abdominal binder, mastectomy binder, or other means of securing the device to the patient. Additionally, an insulator (not illustrated) may be attached to the external surface of the rear device housing 23 to protect the patient/user from any excess heat generated by the device itself during operation. In a further exemplary embodiment, a sound insulator/reduction component or structure to reduce the sound waves generated by the unit may also be attached to the external surface of the rear device housing. The sound insulator/reduction component may reduce both actual sound volume as well as amplitude thereof, in order to provide a more comfortable situation for the patient/user.

Figure 6:
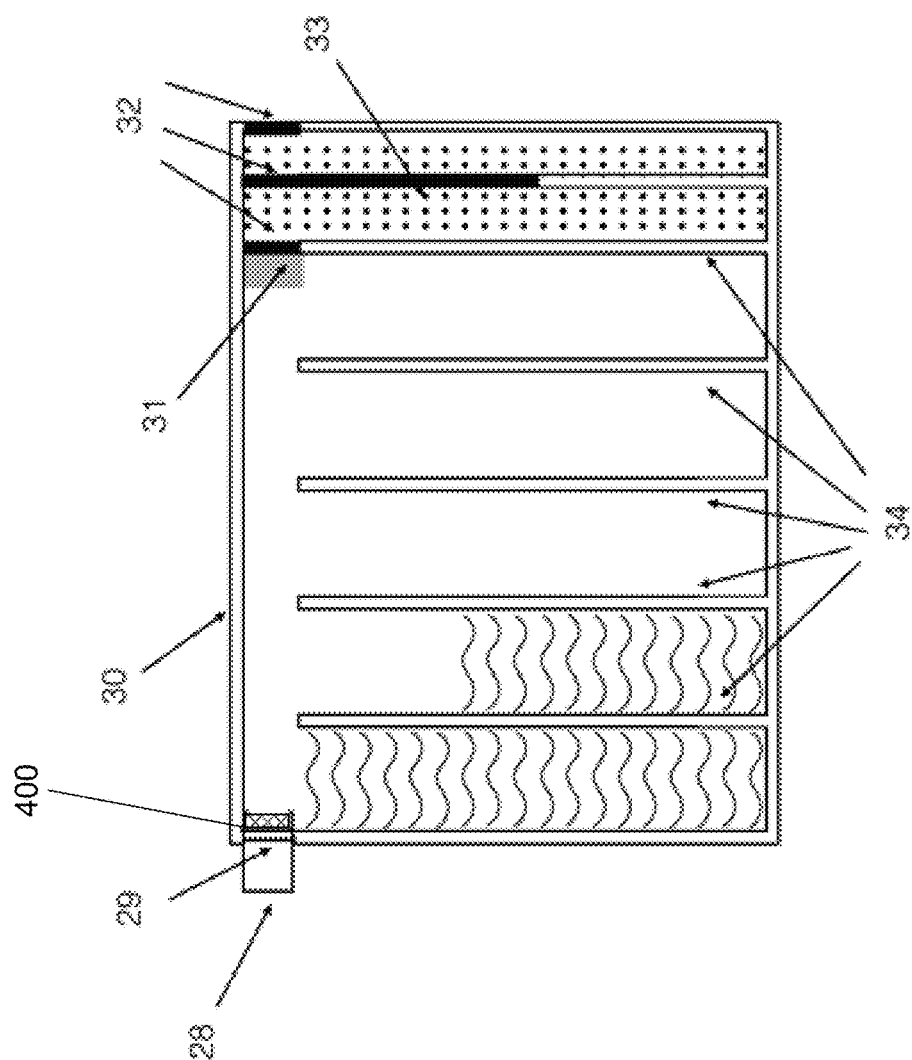
FIG. 6 is a perspective view of one embodiment of the fluid reservoir.

FIG. 6 shows a cutaway view of an embodiment of the reservoir. The reservoir is compartmentalized by segmenting structures 34 (in the case of a rigid reservoir) or by the heat-sealed or pressed structure (in the case of a flexible pouch-like reservoir). These segmenting structures prevent the splashing or excessive or irregular movement of fluid 200 in the reservoir, and provide a sequential filling order of the reservoir to limit the amount of fluid present in the final segment, in which gas-permeable, liquid-impermeable membranes 32 allow the escape of air. Fluid 200 is transferred from the pump unit into the reservoir through a quick-release connection 28. A one-way valve 29 prevents the backflow of fluid when disconnecting the reservoir from the pump unit. A significant distinction between this reservoir and prior art devices is that the reservoir of the present invention is designed to be disposed of and replaced by a new, clean reservoir each time the fluid fills a reservoir. This significantly improves the patient experience in that they no longer must empty the drain reservoir and replace it.

At the end of the reservoir furthest from the intake connection 28 is a chamber which may contain some compound 33, such as activated carbon, which both hinders the flow of fluid should it gain entry to the chamber, but also removes any odor from the air which is to be released from the reservoir. A mesh (foam or otherwise) filter 31 prevents excess fluid from backing up against the first gas-permeable, liquid-impermeable membrane 32. The end segment is constructed in such a way as to maximize gas release, and minimize the leakage of fluid. In the embodiment shown, three sequential membranes 32 are utilized in order to prevent the escape of fluid from the reservoir.

Additionally, the reservoir may make use of an onboard system (electronic or otherwise) for measuring certain characteristics of the collected fluid. These characteristics may include, but are not limited to, the following: total collected amount; rate of fluid collection on the time scales of hours, days, or weeks; presence of infectious materials; and any other chemicals or substances which may indicate infection; or the presence of some medical condition which may naturally arise in response to the surgical procedure, initial pathology, or additional complications (of either the surgical procedure or the initial pathology) in the fluid collected from percutaneous (internal) wounds.

For example, in one embodiment the reservoir may make use of a fluorescent-based assay for detecting the presence of bacteria, by using a photosensitive sensor to detect the light emitted by excitation of the fluorescent compound in the presence of bacteria. The reservoir may also make use of external graduation markings in combination with a transparent material to allow easy monitoring of fluid collection. Furthermore, in the case of a flexible reservoir design, the reservoir may comprise an internal pouch and an external rigid structure. As the pouch expands and reaches its maximum fill level, it may actuate a limit switch or proximity switch indicating the reservoir is nearing total capacity.

Figure 7:
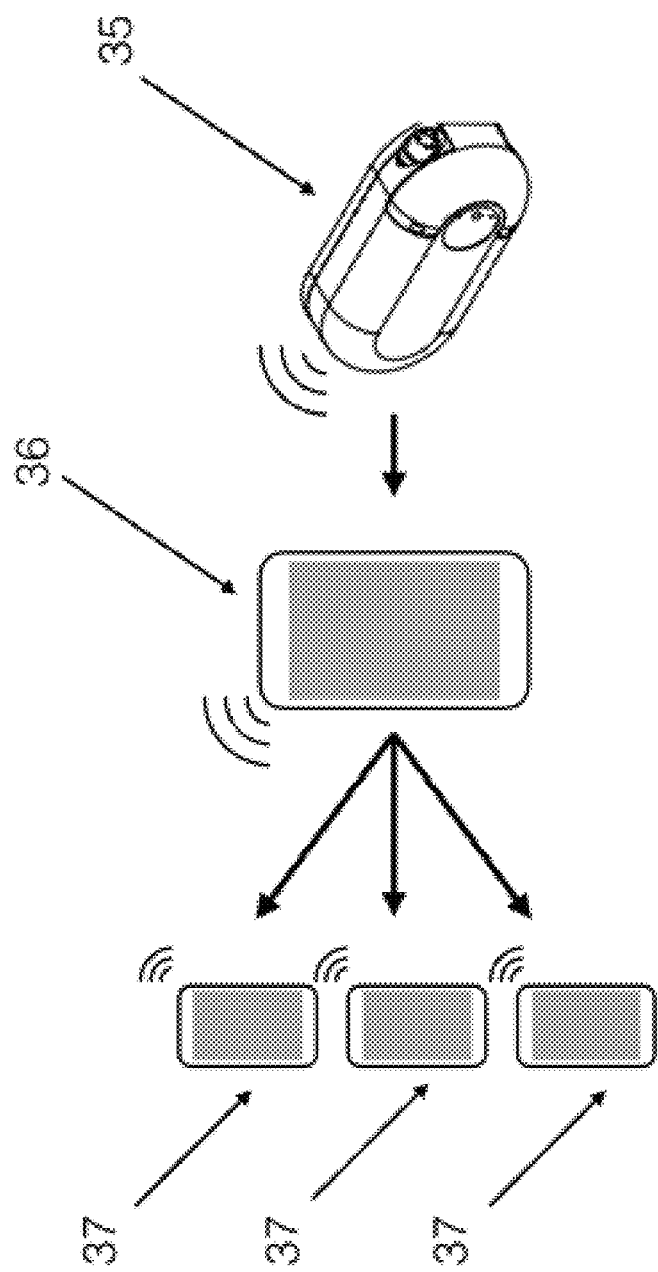
FIG. 7 is a schematic of one embodiment of the device communication features.

FIG. 7 shows a schematic of one embodiment of a communication channel between the pump device 35 and the devices 35, 36 of the staff of an inpatient or outpatient medical center, the patient, their nurse, their doctor, their caregivers, their family, or any interested party as allowed by law. This communication is designed to relay information regarding the function of the device, or the characteristics of the collected fluid, as described previously. The pump device 35 communicates wirelessly with the patient's mobile device 36, tablet computer, or personal computer by either device-to-device communication or by utilizing a local wireless local area network or a cell network. The information received by the patient's device is then relayed in a like fashion (device-to-device, wireless local area network, cell network) to the mobile devices 37, tablet computers, or personal computers of the staff of an inpatient or outpatient medical center, the patient's nurse, their doctor, their caregivers, their family, or any interested party as allowed by law. Any of these devices, or the pump device itself, may make treatment recommendations or diagnoses based on the information gained from the collected fluid.

Figure 8:
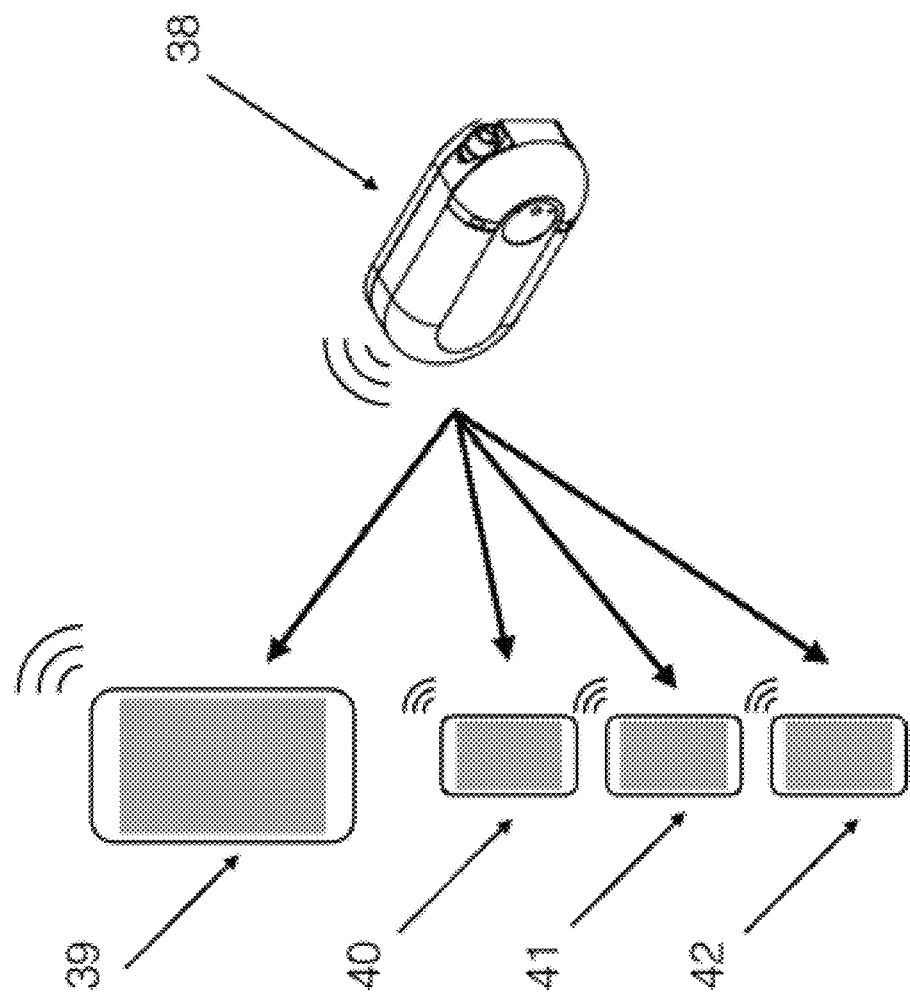
FIG. 8 is a schematic of a different embodiment of the device communication features.

FIG. 8 shows another embodiment of a communication channel between the pump device 38 and the devices 39, 40, 41, 42 of the staff of an inpatient or outpatient medical center, the patient, their nurse, their doctor, their caregivers, their family, or any interested party as allowed by law. This communication is designed to relay information regarding the function of the device, or the characteristics of the collected fluid as described previously. The pump device 38 communicates wirelessly with the mobile devices, tablet computers, or personal computers of the staff of an inpatient or outpatient medical center, the patient 39, the patient's nurse, their doctor, their caregivers, their family, or any interested party as allowed by law 40, 41, 42. Any of these devices, or the pump device itself may make treatment recommendations or diagnoses based on the information gained from the collected fluid.

Figure 9:
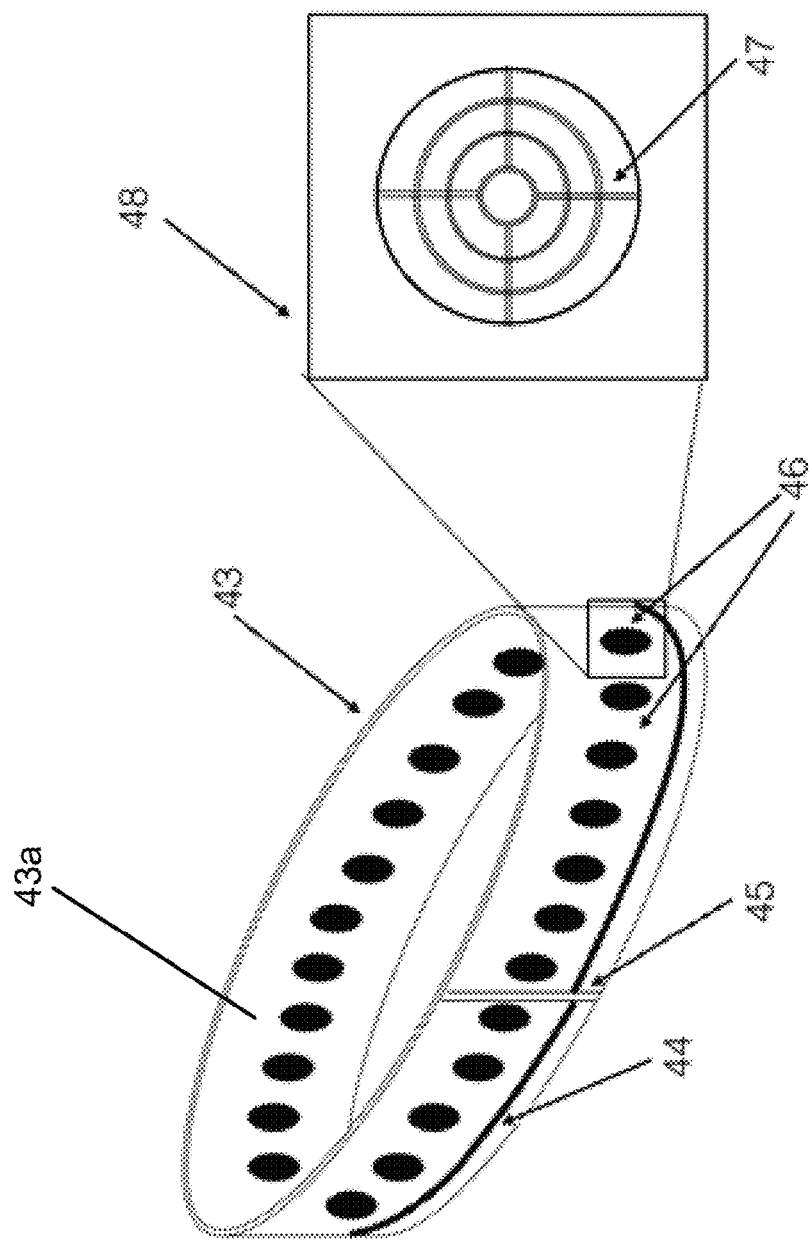
FIG. 9 is a perspective view of one embodiment of a device used to fasten the device to the patient (e.g., abdominal binder, mastectomy bra, and the like).

FIG. 9 is a perspective view of an exemplary embodiment of an apparatus 43 which may function as an abdominal binder, mastectomy bra, or any other means of attaching the pump device and reservoir to the patient. The apparatus 43 is constructed from fabric or other suitable material, and is backed with a padding or other material 43a which increases the comfort to the patient, such as, but not limited to, foam or gel padding. A series of ports 46 which allow the drainage tubing to pass through the apparatus are provided at various locations around the apparatus, and may be present in a repeating pattern or spacing. The apparatus may incorporate a greater or lesser number of these ports than shown in FIG. 9.

A tubing channel 44 is provided in the apparatus to allow convenient routing of the drainage tubing. This channel may secure the tubing by means of folding a section hook-and-loop fastener fabric over the tubing along the length of device or portions thereof. The channel also may comprise several snap-fit clamps along the length of the apparatus.

A magnified view 48 of the pass-through ports 46 shows in detail the construction of the port. The port comprises a foam portion which has been pre-punched or pre-cut 47 in such a way as to allow easy removal of the section of foam which has a diameter close to the diameter of the desired drainage tubing. By incorporating this feature, surgeons may make use of any diameter drainage tubing, or may utilize several different sizes of tubing at different locations.

A fastening feature 45 allows the apparatus to be removed easily. The feature may function by means of hook-and-loop fabric, button snaps, buckle fasteners, or clasps. The apparatus may also include some feature for mounting the pump and reservoir, or any other desired peripheral devices. This feature will match a corresponding feature on the pump and reservoir to allow quick and easy removal, in a manner similar to that described above. The device also may feature some other means of securing the drainage tubing.

Figure 10:
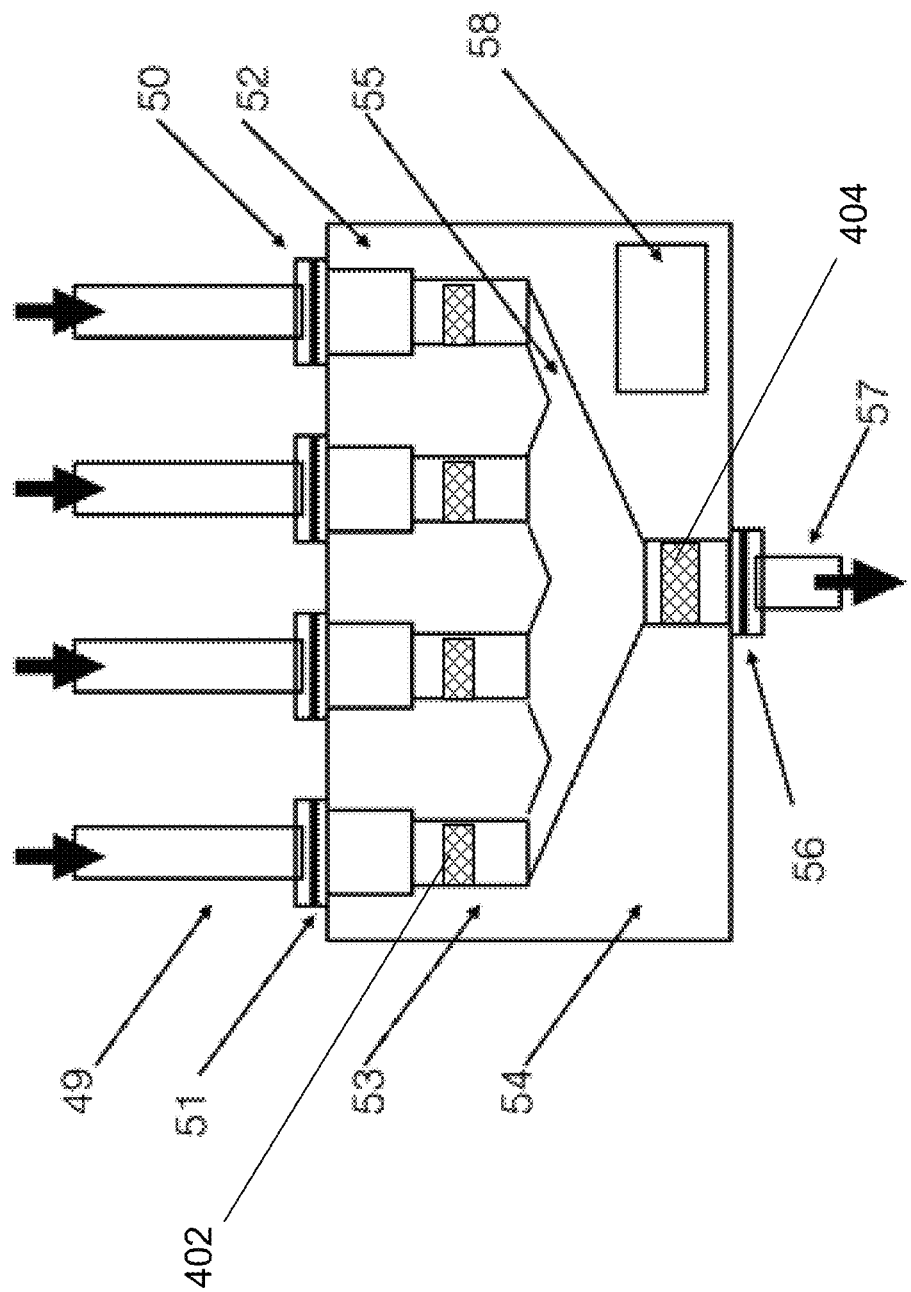
FIG. 10 is a cutaway view of one embodiment of the multiple tubing input manifold.

FIG. 10 is a cutaway view of one embodiment of the manifold at the pump entrance. This manifold allows the connection of one or many drainage inputs. In this embodiment, four input connections are shown; however the manifold may comprise fewer inputs or greater inputs. Each drainage tubing line 49 is secured to the manifold by a connector 50 (which may be a barbed fitting and quick-disconnect combination). This connector 50 may allow for the input of many different sizes of drainage tubing via adaptor fittings or through inherent design. Downstream of the connector is a one-way valve 51 which prevents backflow of the fluid.

Within the body 54 of the manifold are channels 52 which accept the fluid after the one-way valve 51. These channels 52 direct the fluid into separate measurement units 53 which collect information about the characteristics of the collected fluid. These characteristics may include, but are not limited to, the following: total collected amount; rate of fluid collection on the time scales of hours, days, or weeks; presence of infectious materials; and any other chemicals or substances which may indicate infection, or the presence of some medical condition which may naturally arise in response to the surgical procedure, initial pathology, or additional complications (of either the surgical procedure or the initial pathology) in the fluid collected from percutaneous (internal) wounds. This information may then be relayed to an onboard processor 58 for additional processing before being forwarded on to the processor in the pump device. A collection unit 55 channels all fluid into single channel. The manifold may include another one-way valve 56 at the exit 57 which may make use of a quick-disconnect connector or may transfer the fluid directly the pump unit. In this embodiment, the manifold, itself, does not possess any means of moving the collected fluid but rather relies on the action of the downstream pump device. The manifold may be separable from the pump device or may be a continuous molded unit with the body of the pump device.

Figure 11:
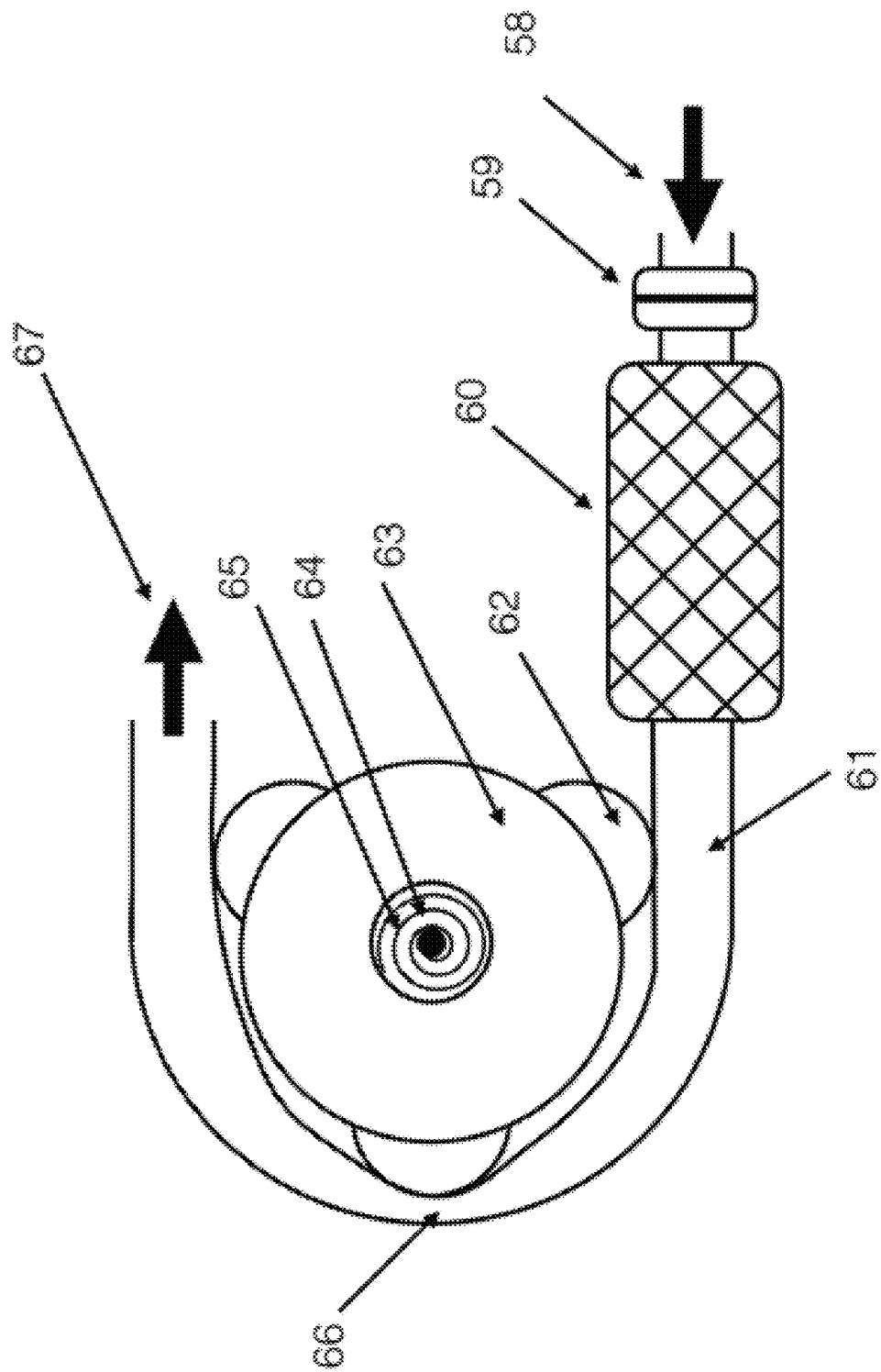
FIG. 11 is a view of one embodiment of a mechanism to prevent excess pressure for building up against the outlet one-way valve.

FIG. 11 shows an overview of a unique mechanism within the peristaltic pump device which prevents a high pressure in the system downstream from the central rolling unit 63. This is useful particularly when the reservoir is removed from its connection to the upstream collected fluid. A one-way valve or valves may be positioned both before and after the reservoir connection, and the upstream valve likely will have some residual pressure against it which may cause an amount of fluid to leak when the reservoir is disconnected. This mechanism allows the central rolling unit to automatically reverse, i.e., turn in a direction opposite the direction it must turn to normally pump the fluid. This is achieved via a spring 65 at the attachment between the motor output shaft 64 and the body of the central rolling unit 63. When the motor is stopped the spring naturally unwinds or uncoils, causing the central rolling unit to turn with it some amount. This causes the point at which the rollers contact the tubing 66 to shift, causing the fluid to be pushed backwards opposite its normal flow direction. A section of compliant tubing 60 allows the influx of excess fluid without causing a higher than optimal pressure to develop in the tubing. A one-way valve 59 prevents the fluid from back flowing through the pump entrance 58. The arrows 58 and 67 show the normal direction of fluid transport. The direction of fluid transport caused by this mechanism (when the motor is stopped) is opposite the direction denoted by the arrows. Not shown is the pump housing, which holds all components and allows the peristaltic action of the pump.

Figure 12:
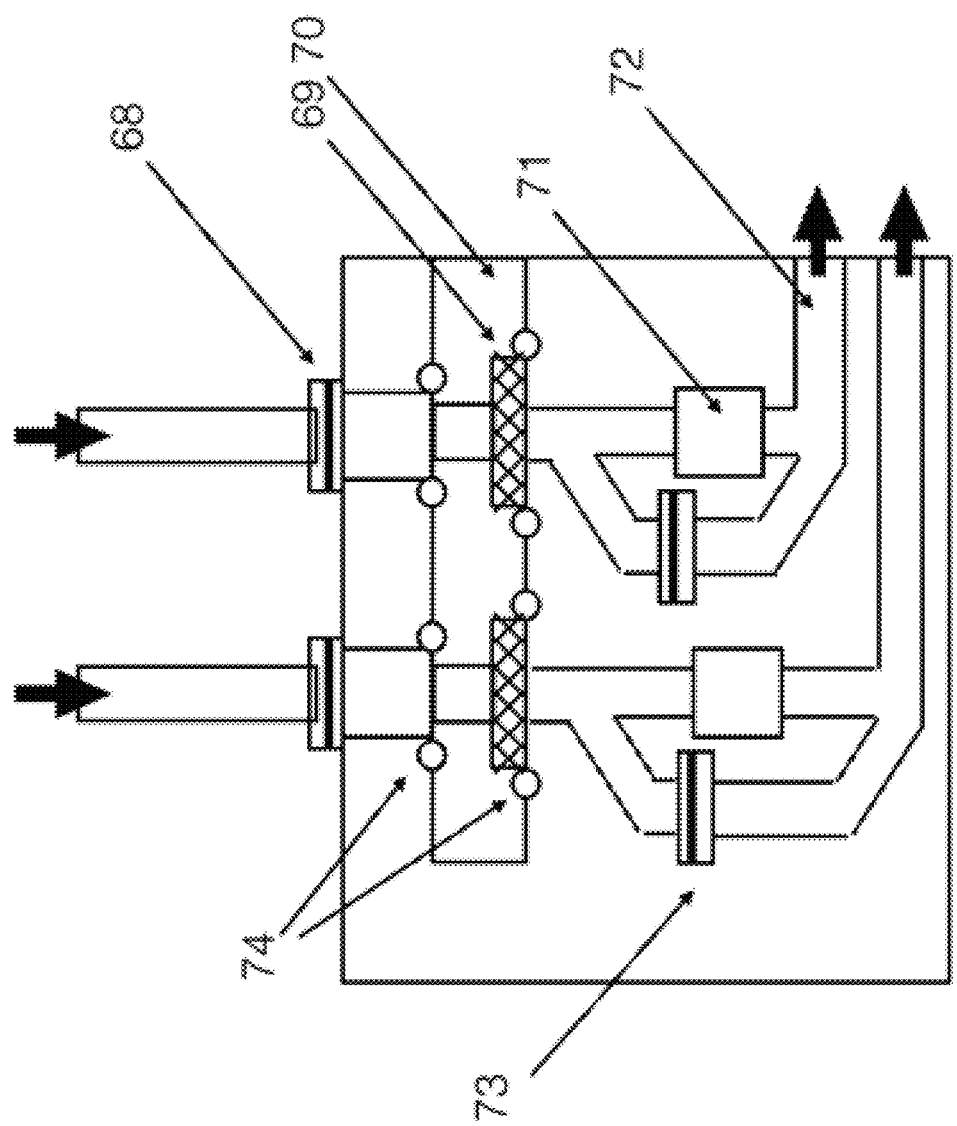
FIG. 12 is a view of one embodiment of a mechanism to allow the preservation of the "stripping" or "milking procedure", and also allows for the collection of large materials which may be problematic for the pumps in the device.

FIG. 12 is an overview of one embodiment of a mechanism to allow the preservation of a "stripping" or "milking procedure", and also allow for the collection of large materials, which can cause problems in the pump(s). The "milking" or "stripping" procedure is currently prescribed as a method to clear blockage in the drainage structure, and calls for the user to apply pressure using their fingers to the tubing above the blockage and, in a peristaltic nature, moving their fingers down the tubing past the blockage, promoting a restored flow. As several exemplary embodiments of the present utilize a peristaltic pump, which occludes flow if stopped, some mechanism is needed to accommodate the "stripping" or "milking" procedure. This mechanism consists of one or more one-way valves 68 (generally one per drainage connection) immediately after the connection to the drainage structure, which prevents backflow of fluid or particles into the tubing. Immediately downstream of the one-way valve is a chamber (or chambers) 70 to receive fluid and particles, the latter of which may potentially block downstream components in the device and inhibit flow. At the exit of this chamber is a filter or screen 69, which prevents larger particles from moving further downstream. This entire chamber may be removable, in which case seals 74 are incorporated to prevent fluid leakage by occluding the gap necessary to facilitate removal of the chamber. Downstream of this chamber, the tubing bifurcates with one channel facilitating fluid transport to the pump(s) 71 and a second "bypass" channel facilitating fluid transport around the pump when the "milking" or "stripping" procedure is performed. A one-way valve 73 is placed in the second channel to prevent backflow of fluid during normal pump operations. The valve remains closed, and the bypass channel thus is shut-off to fluid flow during normal operations. The two tubing channels converge to a single channel downstream from the pump and one-way valve, facilitating fluid transport to the remainder of the device 72 or to the output reservoir.

Figure 13:
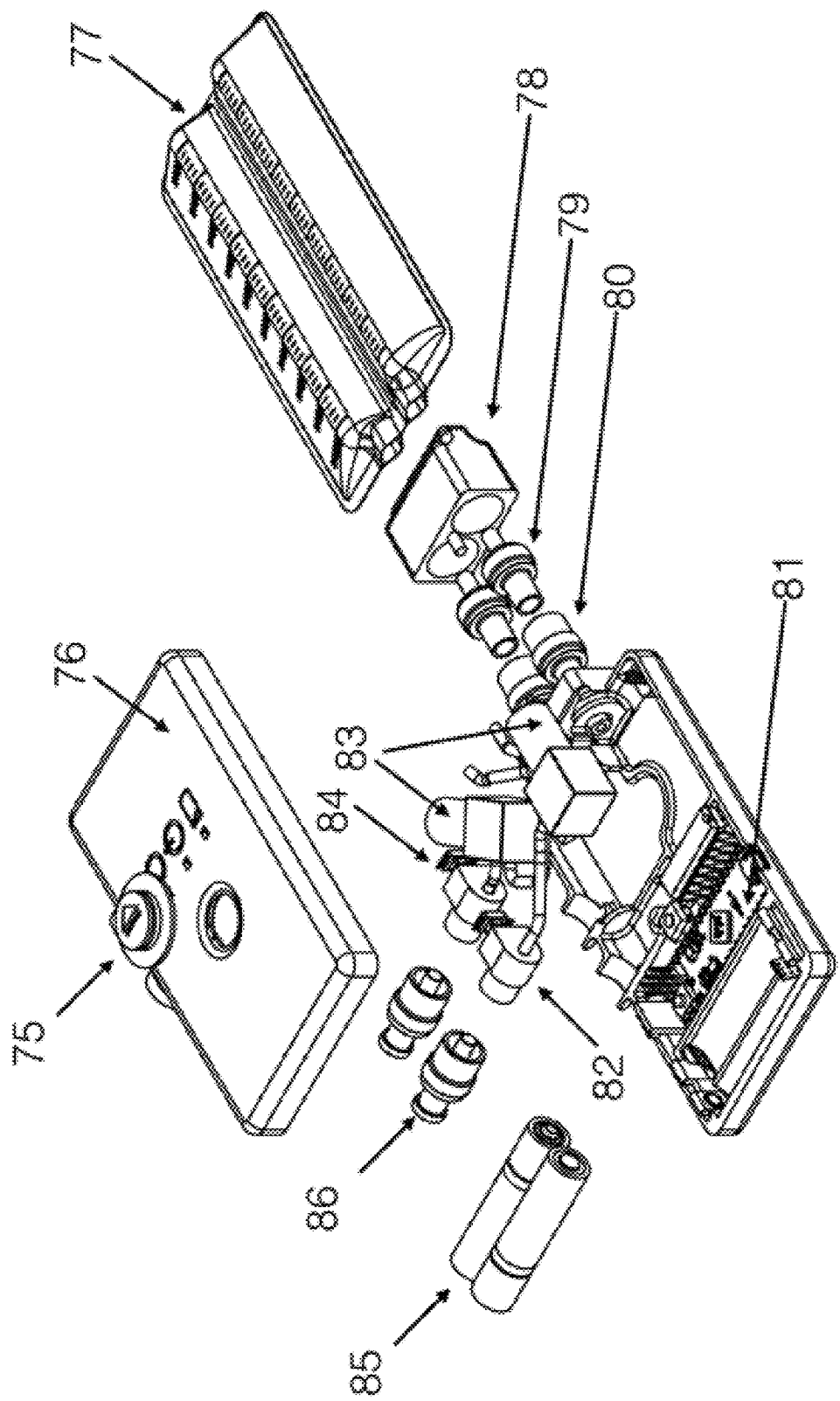
FIG. 13 is an exploded view of one embodiment of the device described in this document.

FIG. 13 is an exploded view of an exemplary embodiment of an assembled device incorporating the elements described above. Fluid inlet connectors 86 (either barbed or otherwise) allow for the connection of one or multiple drainage structures or tubes (as described above) to the pump unit of the device. In this embodiment, two drainage structures are accommodated; however, additional structures may be provided for by including additional assemblies of the relevant components. For each fluid inlet, immediately downstream of the connector is a one-way valve, as described above, to prevent the backflow of material into the drainage structure. Downstream of the one-way valve is a fluid chamber 82, which includes a pressure sensor 84 to monitor the pressure developed in the device. Tubing allows fluid from this chamber to flow into a peristaltic, or positive displacement, pump 83, which applies negative pressure on the upstream side of the pump, and positive pressure on the downstream side. This positive pressure downstream of the pump causes fluid to be transported through the remainder of the pump housing body and connection elements to a reservoir unit 77.

A set of one-way valves 79, 80 may be incorporated at the connection between the pump housing body and the reservoir to prevent fluid leakage during change of reservoirs. The reservoirs may be collapsible in nature which are much more comfortable to the patient, and may be made in a more economic, and environmentally conscious, way as the collapsible reservoir will necessitate a smaller volume of plastic to produce. The reservoir incorporates some means of removably attaching to the pump body, which allows the reservoir to be conveniently detached and replaced by the patient. In this embodiment, a connector 78 is attached to the reservoir, which mates to a counterpart receptor on the pump housing body.

As seen in FIG. 13, the reservoir unit comprises a pair of independent reservoirs as described above. The reservoir thus may contain several channels to allow the fluid from multiple drainage structures to be independently collected. These may be necessary if the healthcare professional desires to independently record the collected fluid amounts. Furthermore, the reservoir may be graduated, either by adhering a label or paint to the reservoir, or by embossing the plastic. These graduations allow the fluid collected fluid amount to be easily assessed.

The reservoir may also contain a substance intended to sterilize the collected fluid, and may also cause the fluid to congeal. This is necessary for the reservoir to be disposed of as "white bag" waste, or waste which may be disposed of in landfill without additional treatment. This substance may be contained in a pouch or container within the reservoir or may be freely distributed inside of the reservoir. This pouch or container may be ruptured by the patient in order to disburse the contents, or may simply dissolve within a convenient period of time.

The reservoir or manifold, or both, may further comprise one or more sensors or measurement devices 400, 402, 404, internally or externally, or both. These sensors provide diagnostic value in taking various measurements associated with the collected fluid. Measurements can include and are not limited to collected fluid amount, pH, certain known harmful mediators (cytokines, chemokines, reactive oxygen species), protein levels, blood content, etc. For example, amount of fluid collected can be an indicator of possible seroma development in some hernia surgeries. Additionally, pH has also been shown to act as an indicator of possible seroma formation. The present invention thus allows for the detection of infectious materials, and any other chemicals or substances which may indicate infection, or the presence of some medical condition which may naturally arise in response to the surgical procedure, initial pathology, or additional complications (of either the surgical procedure or the initial pathology) in the fluid collected from percutaneous (internal) wounds. Sensors may also be located in the pump unit.

Detection of a full reservoir may be accomplished by counting the revolutions of the peristaltic pump, or cycles of the positive displacement pump, and then calculating the total displaced fluid. This is made possible because the peristaltic, or positive displacement pump moves a nearly constant amount of fluid or gas with each revolution of its motor. The device may be powered by either consumable or rechargeable batteries 85 which are held in a battery holder.

A circuit control board 81 comprising some or all required electrical components controls the operation of the device. The control board may take as inputs, and make decisions regarding, the following: user inputs via interface buttons; battery charge level; need to change reservoir; device temperature; current magnitude of negative pressure; presence of blockage in tubing; or the characteristics of the collected fluids. These characteristics may include, but are not limited to, the following: total collected amount (either total or per drainage structure); rate of fluid collection (total or per drainage structure) on the time scales of hours, days, or weeks; presence of infectious materials; and any other chemicals or substances which may indicate infection, or the presence of some medical condition which may naturally arise in response to the surgical procedure, initial pathology, or additional complications (of either the surgical procedure or the initial pathology) in the fluid collected from percutaneous (internal) wounds.

The user interface may comprise a single push-button 75, which controls an on/off or pause function, as well as any other functions which are desirable for the operation of the device. One operation may be the selection of desired level of negative pressure. The interface may also consist of a series of lights or a screen which alerts the user to various conditions including, but not limited to, device power state (off/on/paused), selected pressure level, battery charge level, need to change battery, reservoir fill level, need to change reservoir, insufficient vacuum seal at any point in the system, or presence of infections materials, and any other chemicals or substances which may indicate infection, or the presence of some medical condition. The device may apply a negative pressure in the range of 50 mmHg to 700 mmHg below ambient pressure either continuously or intermittently, or operate solely in range from 200 mmHg and 700 mmHg below ambient pressure, either continuously or intermittently. The device may create a constant negative pressure of a desired amount and then allow the motors to momentarily stop, until a time when the onboard pressure sensors detect that the applied pressure has fallen below some desired threshold. Alternatively, the pumps may apply pressure based on a time increment rather than a pressure level.

Figure 14:
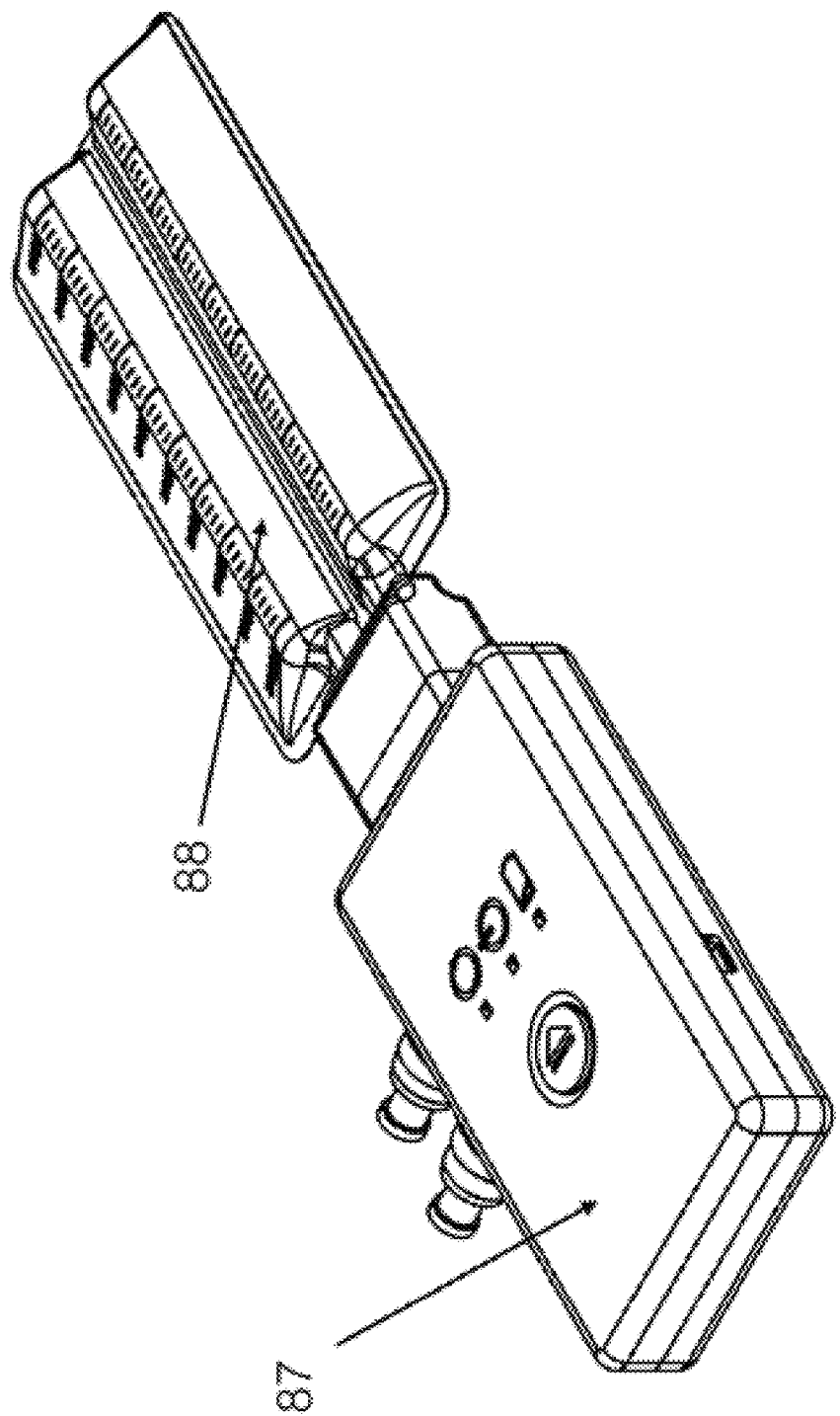
FIG. 14 is an assembled view of one embodiment of a pump unit in accordance with an exemplary embodiment of the present invention.
Figure 16:
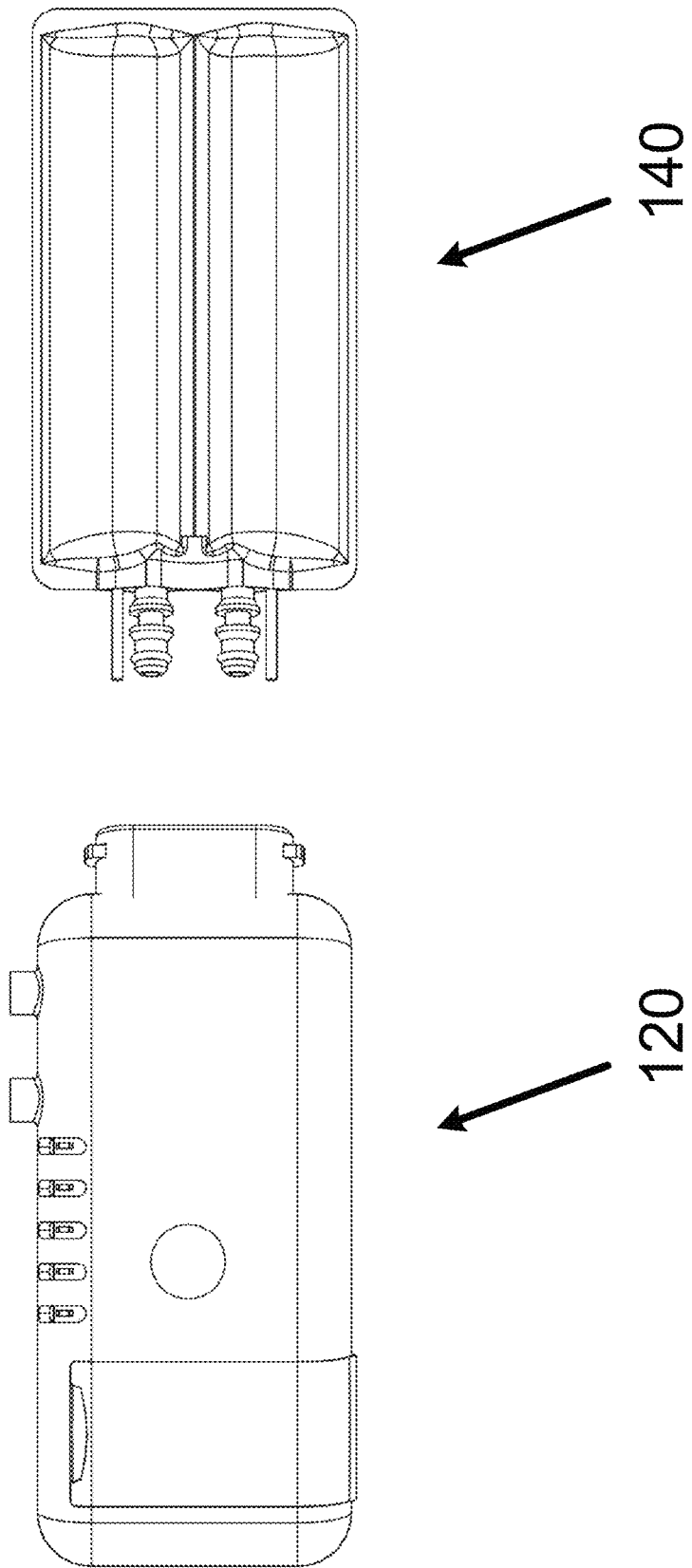
FIG. 16 shows a top view of an alternative embodiment of a pump unit and reservoir.
Figure 17:
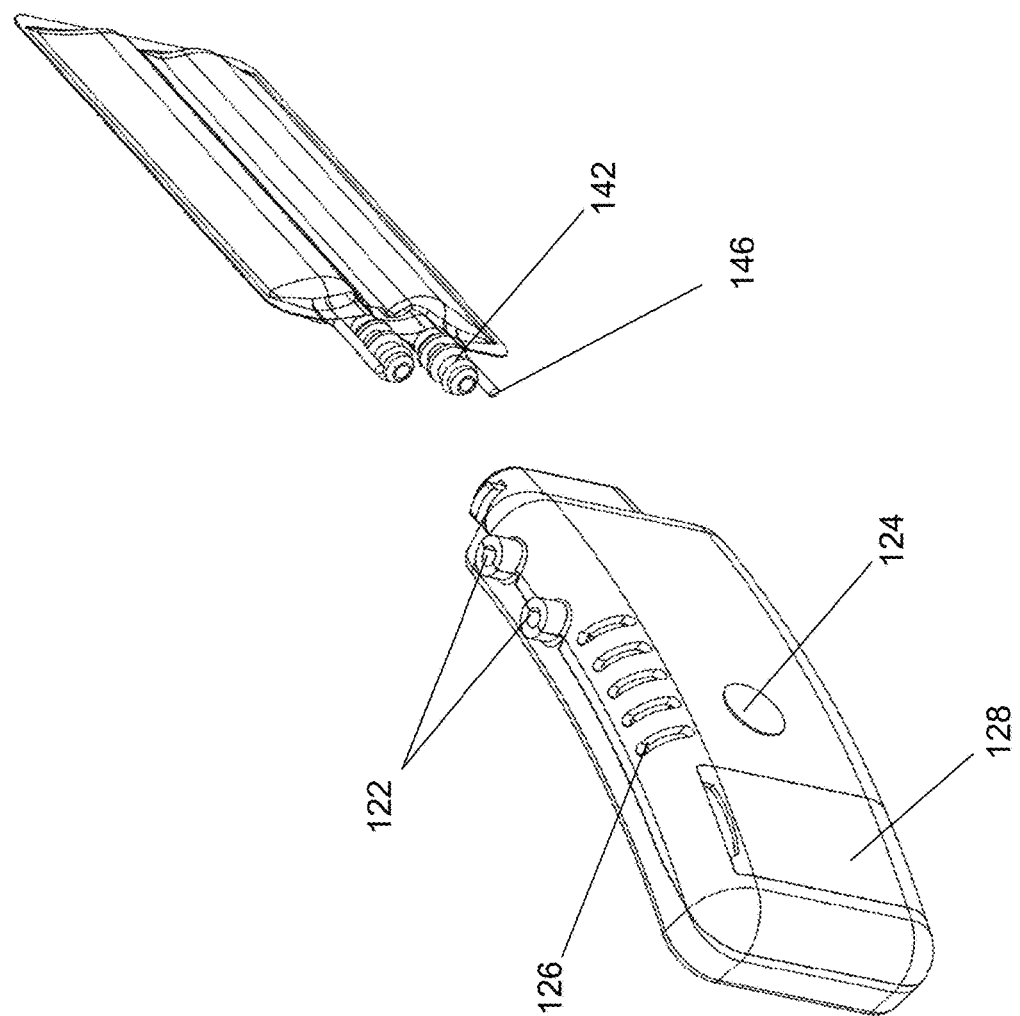
FIG. 17 shows a perspective view of the pump unit and reservoir of FIG. 16.
Figure 18:
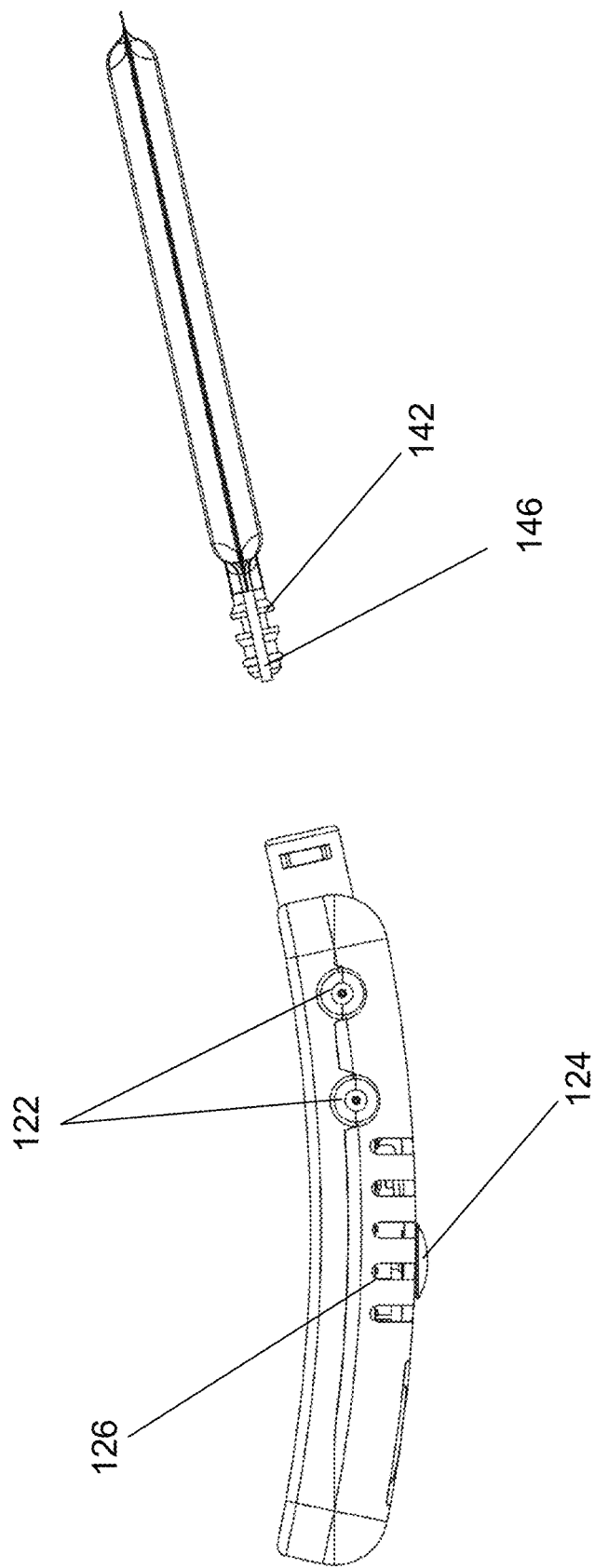
FIG. 18 shows a top view of the pump unit and reservoir of FIG. 16.
Figure 19:
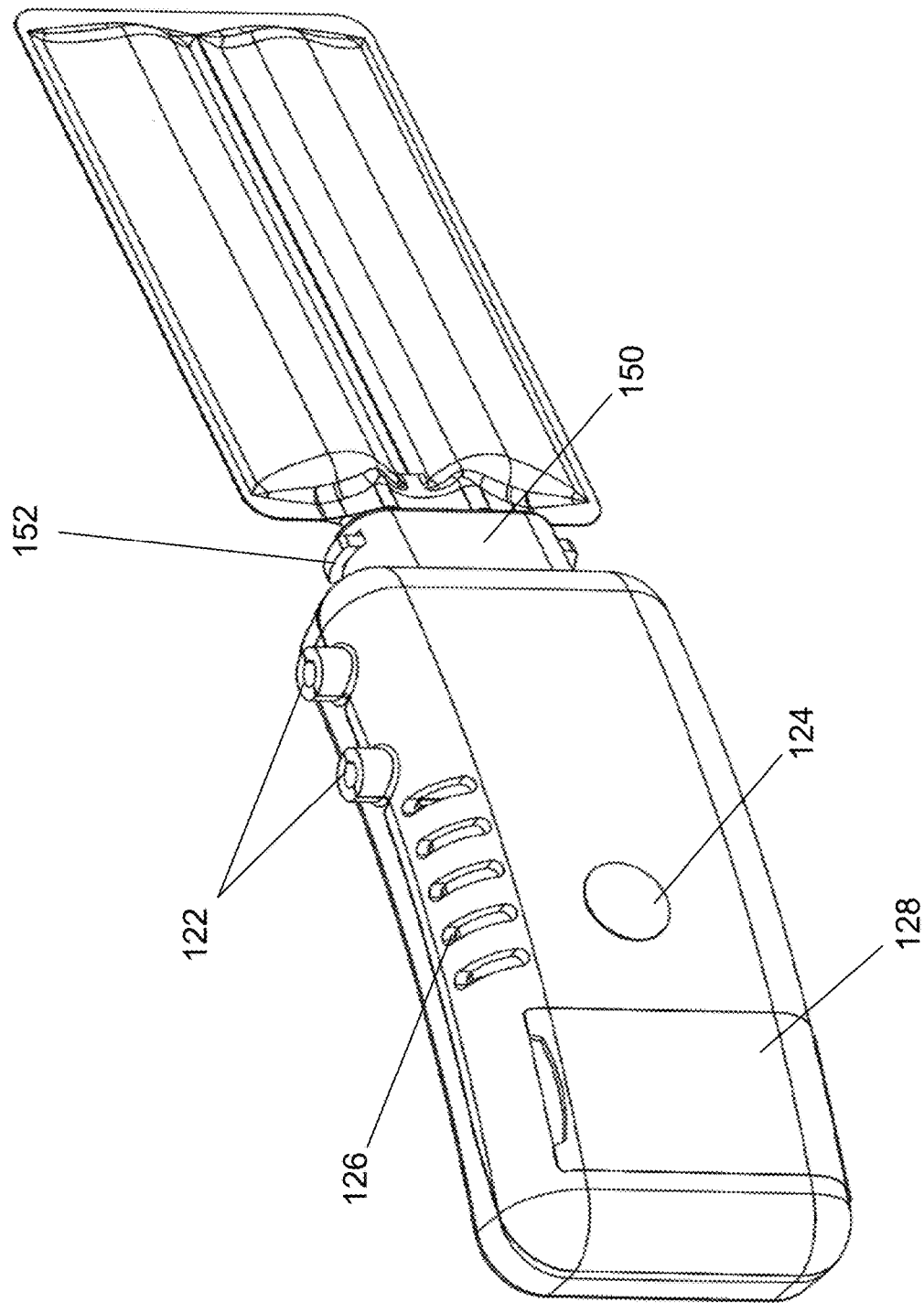
FIG. 19 shows another perspective view of the pump unit and reservoir of FIG. 16.
Figure 20:
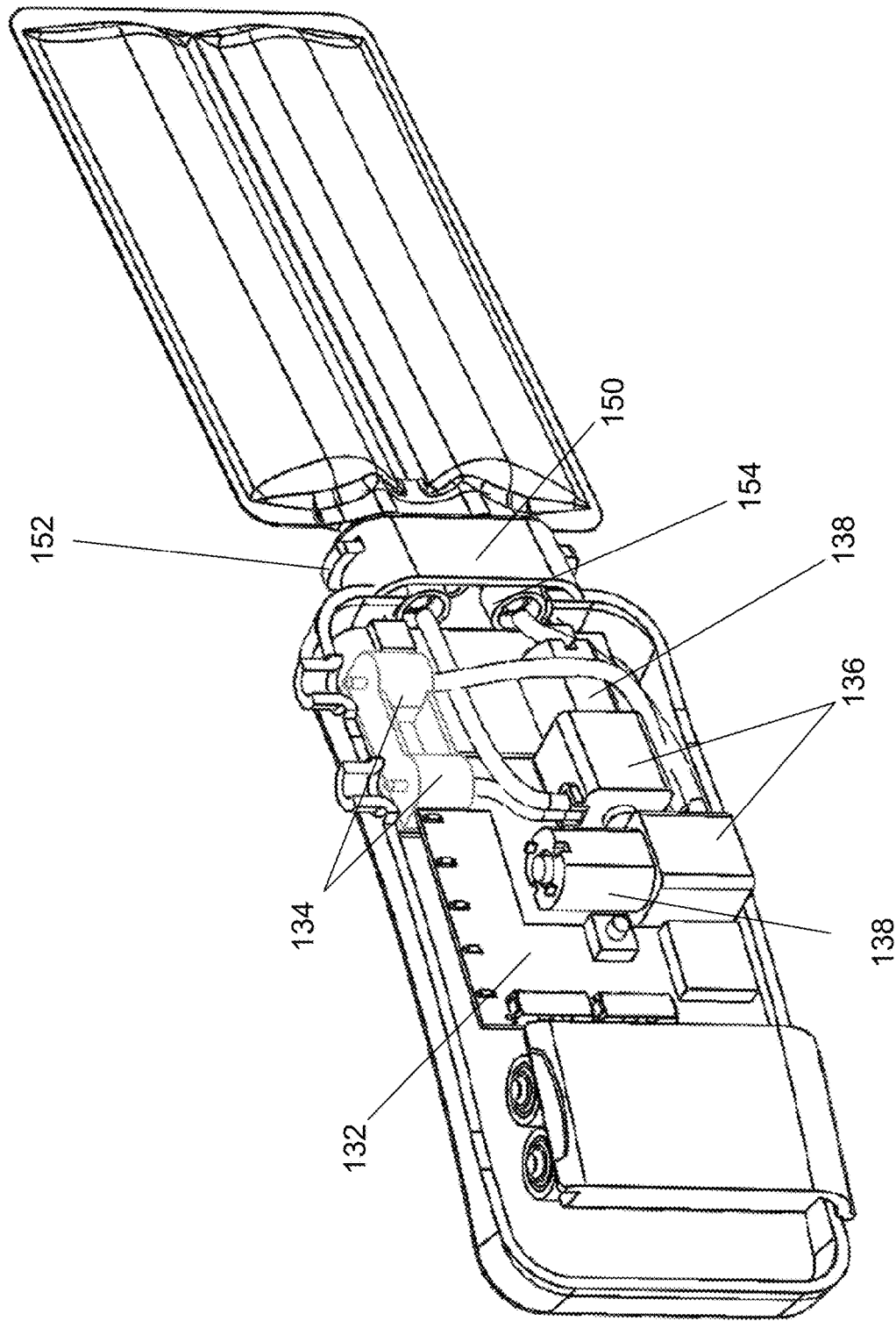
FIG. 20 shows a perspective view of the pump unit with cover removed and reservoir of FIG. 16.
Figure 21:
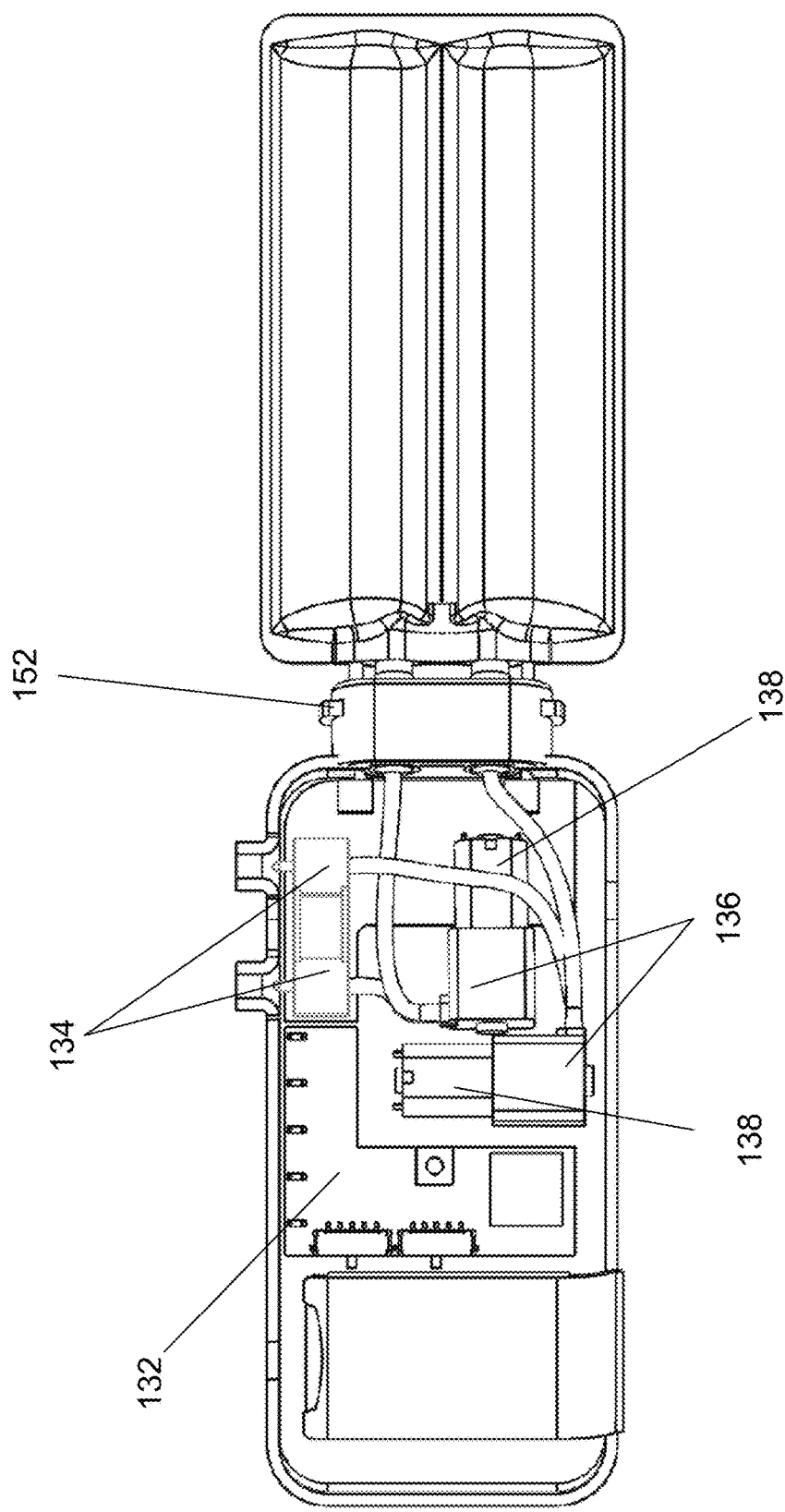
FIG. 21 shows a top view of the pump unit with cover removed and reservoir of FIG. 16.
Figure 22:
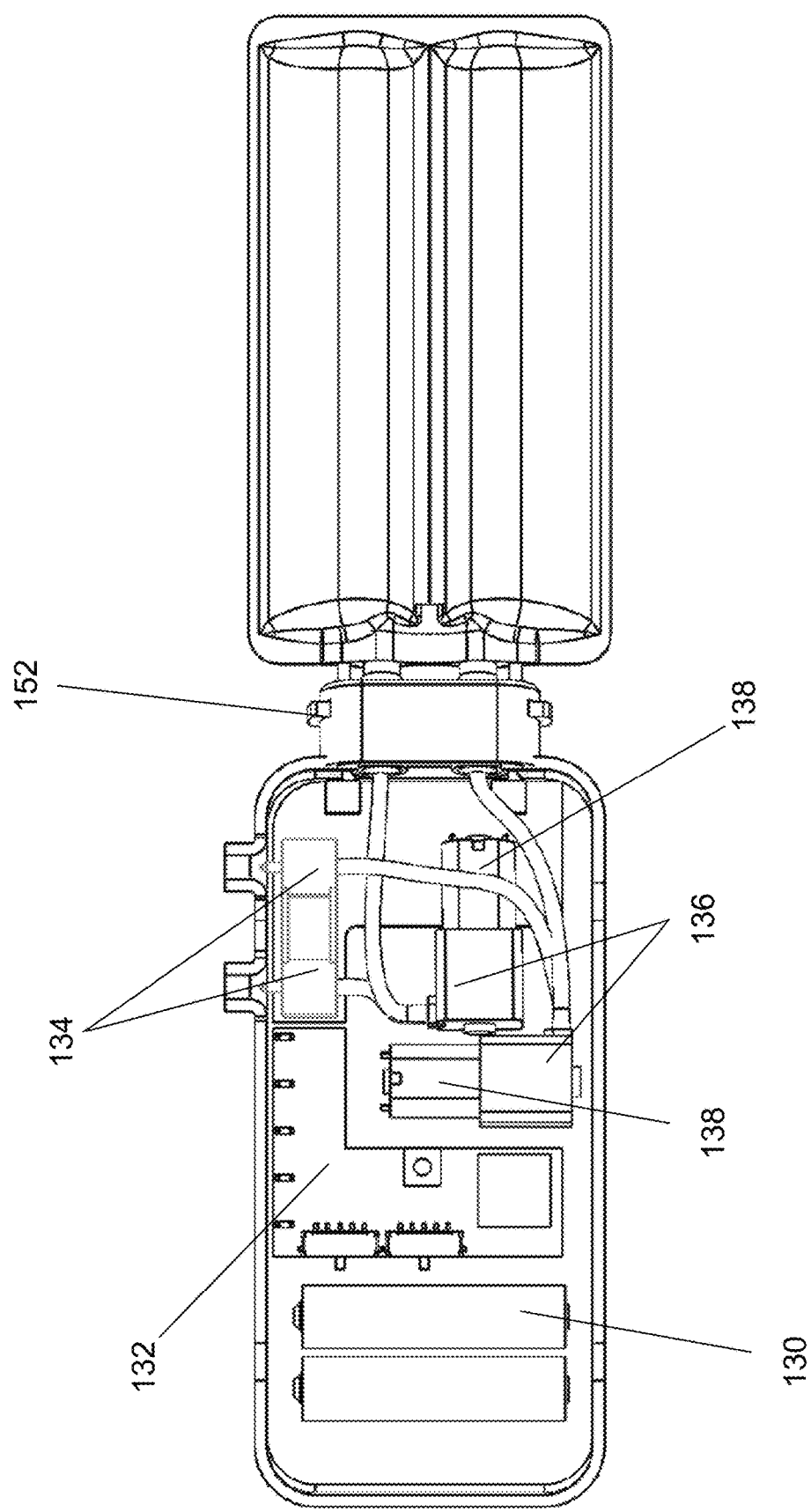
FIG. 22 shows a top view of the pump unit with batteries exposed and reservoir of FIG. 16.
Figure 23:
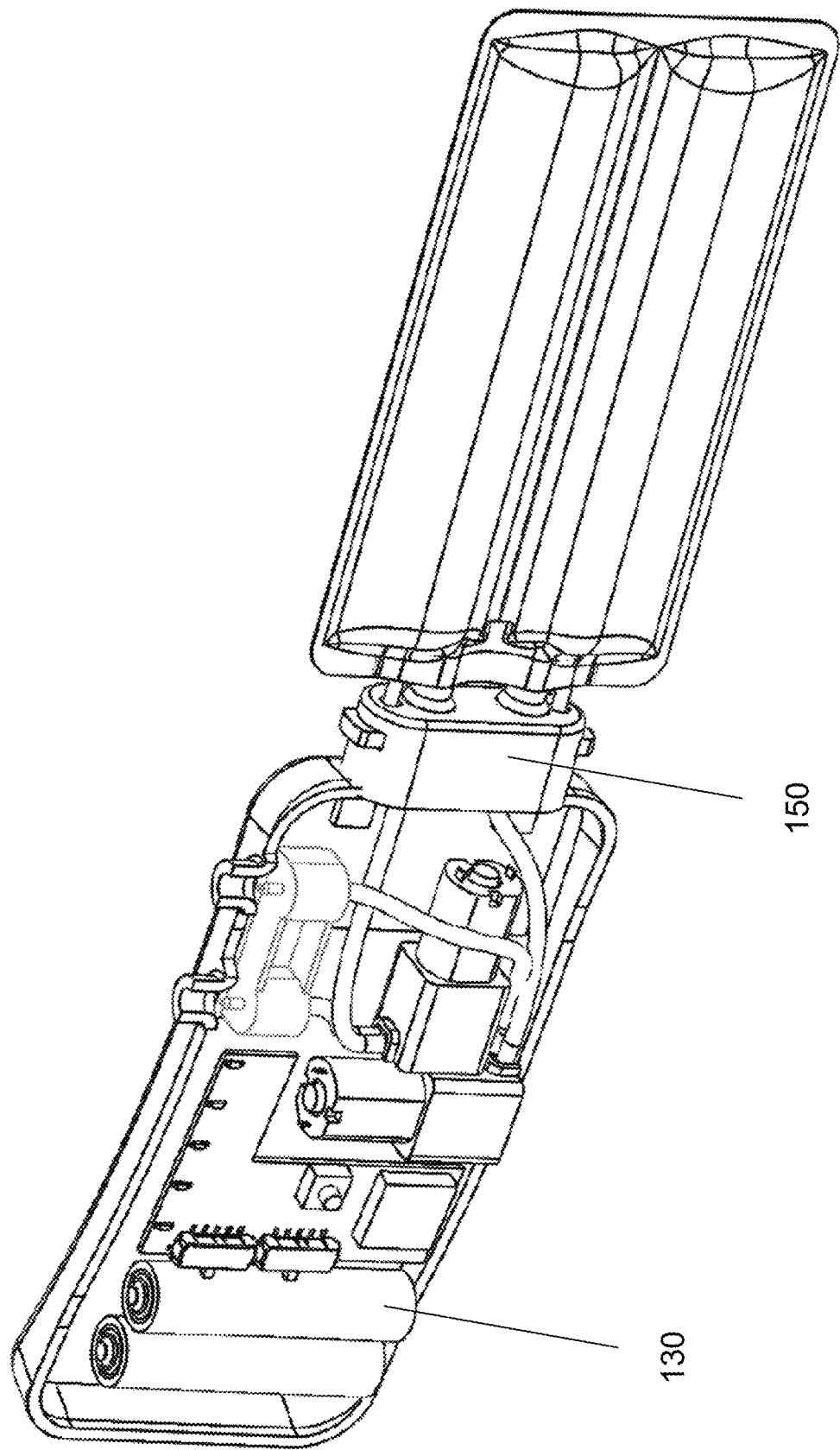
FIG. 23 shows a perspective view of the pump unit and reservoir of FIG. 22.
Figure 24:
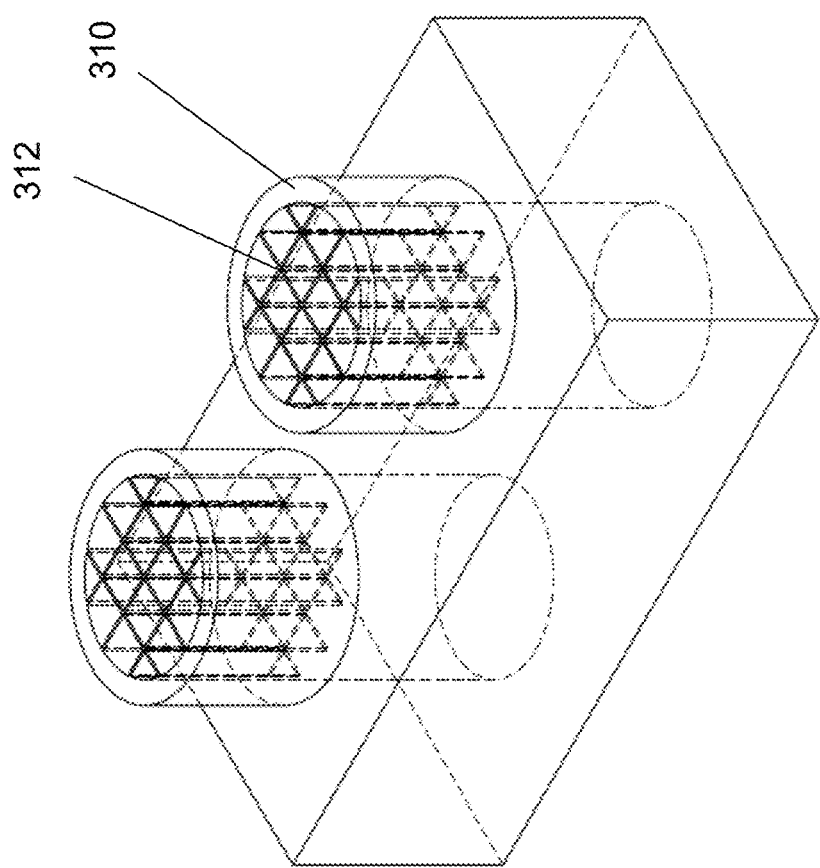
FIG. 24 shows a view of inlet ports with mesh.

FIG. 14 shows a perspective view of the assembled pump unit device 87 and reservoir 88 as detailed above in the description of FIG. 13. In this embodiment, the pump unit is relatively flat and rectangular, with rounded edges and corners.

FIGS. 15A-C show several views of another exemplary embodiment of the assembled pump unit device. In this embodiment, the edges and corners may be more rounded and the entire unit may be curved, as shown. The front or top of the device provides a user interface comprising a single push-button 90, and lights 96 which indicate the status of the unit (which may include but not be limited to on/off, device paused, reservoir full, or faulty tubing connection). The unit may comprise two (or more, as described above) fluid inlets 91, which provide the connection for two drainage structures, and two (or more, to correspond to the fluid inlets) fluid outlets 92, which allow the fluid to be transported to the collection reservoir. As seen in FIG. 15C, the housing 93 is curved in order to conform to the shape of the human abdomen on which the device will be worn. The device may curves not only along the horizontal axis (i.e., length-wise), but also along the vertical axis (i.e., width-wise).

FIGS. 16-23 yet another embodiment of the pump unit 120 and reservoir 140 of the present invention, unconnected and connected. FIGS. 20-23 show the interior of the pump unit (i.e., with the front half of the pump unit housing removed. In this embodiment, the pump unit 120 is curved in a similar manner to the pump unit shown in FIGS. 15A-C. A pair of inlet ports/connectors 122 with one-way valves and inlet fluid chambers 134 are located near one end. A push-button interface 124 is located on the top or front of the pump housing, and a series of lights 126 are located on the side near the inlet ports (which is generally the top side, when the unit is worn). A battery cover 128 allows access to the batteries 130, which provide power to the circuit control board 132 and the pump motors 138. Pumps 136 move fluid to the outlet ports/connectors 154, which are contained in the reservoir holder 150. Pairs of one-way valves 142 extend from one end of the reservoir unit 140 (which contains two independent reservoirs in the embodiment shown), and are inserted into the outlet ports/connectors 154 to attach the reservoir unit to the pump unit. One or more rigid or semi-rigid guides 146 may be provided to fit into corresponding slots or holes in the reservoir holder 150. This establishes connection with a sensor or switch, which enables the control board in the pump unit to determine whether the reservoir unit is attached, as described below. The guides also may help ensure accurate connection and prevent damage to the one-way valves or other connection elements. One or more quick-release tabs or buttons 152 may be provided to allow the reservoir unit to be disengaged and easily removed when pressed.

Figure 25B:
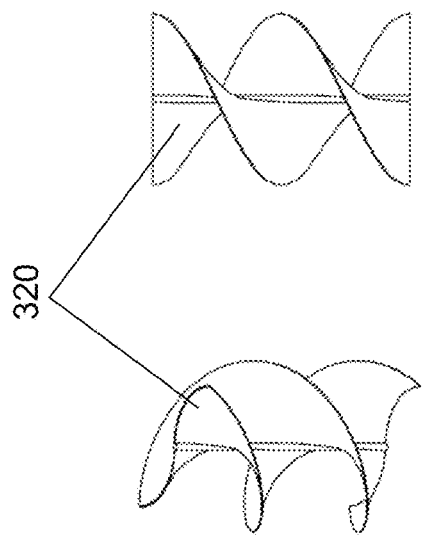
FIGS. 25A-C show views of inlet ports with a rotary blade.
Figure 25C:
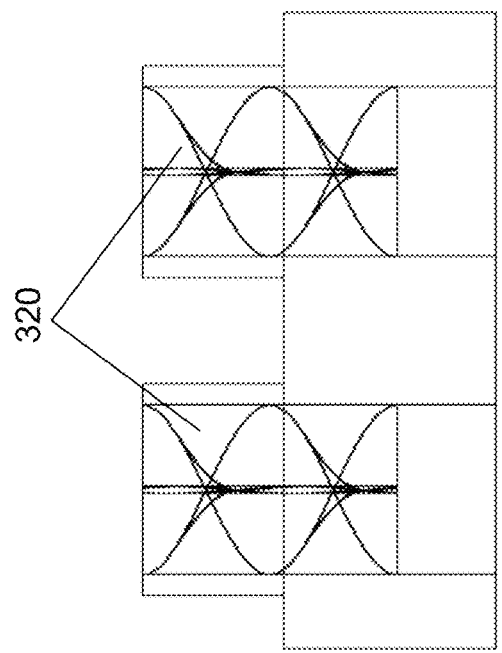
Figure 25A:
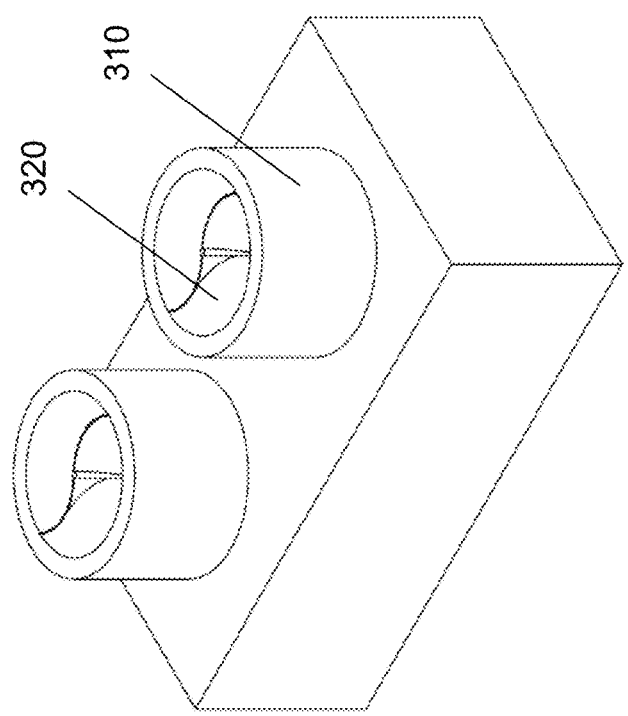
Figure 26A:
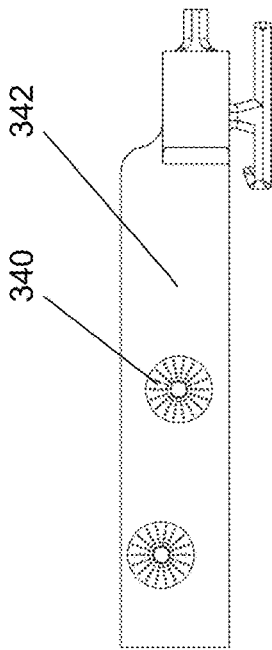
FIGS. 26A-D show views of a reservoir connection unit with integrated filters.
Figure 26C:
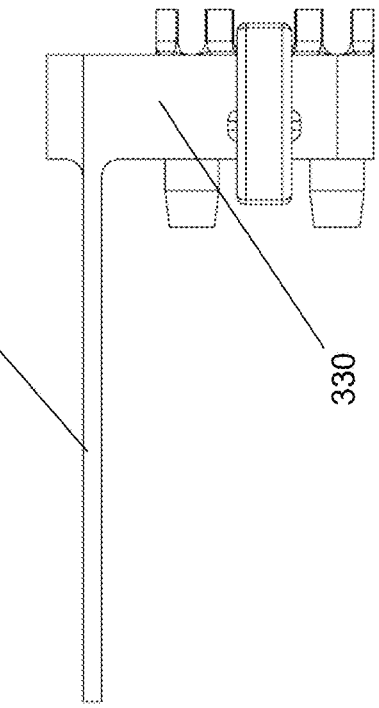
Figure 26D:
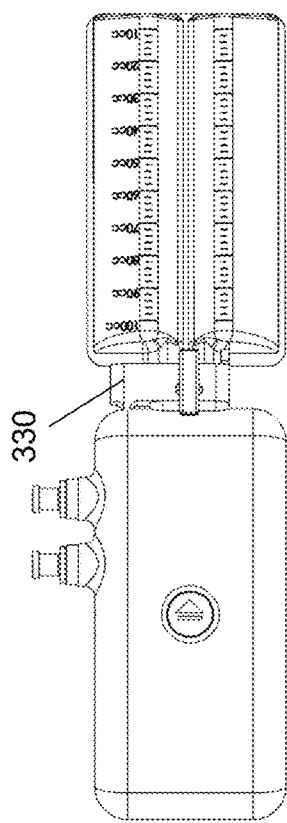
Figure 26B:
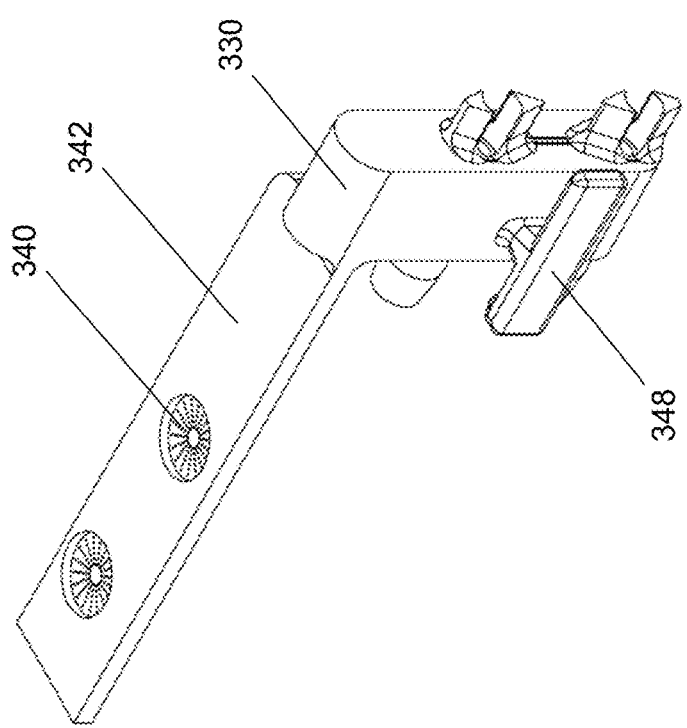

In several embodiments, as seen in FIG. 25, the fluid inlet ports 310 may further comprise a grate or mesh 312, which breaks-up or divides any particles or similar larger material in the fluid which may have been collected during operation. Alternatively, as seen in FIGS. 26A-C, the fluid inlet ports 310 may comprise a rotating blade 320 or rotary apparatus for the same purpose. The blade 320 may spin within the fixed port by either a powered motor or by the power provided by movement of the fluid. In the latter case, the blade has geometry to transform the fluid flow to rotational force, as well as separate geometry to break-up or divide particles or similar larger material as described above.

In yet another exemplary embodiment, filters 340 are provided on a reservoir connection unit 330 which is attached to one end of the reservoir unit 140. When the reservoir connection unit is used to attach the reservoir unit 140 to the pump unit 120, the filter arm 342 with filters 340 is inserted into a slot in the end of the pump unit, so the filters 340 are inserted into the fluid flow lines in the body of the pump unit 120. When the reservoir unit is removed (such as by pressing the quick release latch 348), the reservoir connection unit and filters are also removed. The reservoir connection unit and filters can be disposed of with the reservoir. In one embodiment, the filters or reservoir connection unit, or both, may be removable from the reservoir unit, and cleaned for re-use.

In yet another embodiment of the invention, the reservoir unit prevents re-connection to the pump unit after an initial connection to the pump unit (or other suction apparatus). This prevents re-attachment of a presumably full reservoir unit, and the attempted movement of fluid into a full fluid collection reservoir.

In a further embodiment of the invention, the pump control unit can detect whether a reservoir unit is connected to the outlet ports/connections, and prevents normal operation (i.e., the pumping of fluid) without a reservoir present to contain the fluid. The detection mechanism may comprise a mechanical switch or latch, the formation or breaking of an optical pathway, or similar mechanism appropriate for determining or confirming proximity.

The various embodiments of the present invention thus provide substantial improvements and advantages over the prior art. First, the present invention allows multiple drainage tubes to be connected to the same source of negative pressure. Prior art devices lack the functionality to allow the combination of multiple drainage tubes into a common source of negative pressure, thus requiring patients in surgeries necessitating multiple drains to wear multiple instances of the previously described device. Second, the present invention also places the reservoir after the negative pressure source. Prior art systems require the reservoir to be placed between the tubing leading from the internal wound site and the source of the negative pressure, which impairs functioning of the device. For example, gravity's action on the fluid to provide an air space on which the source of negative pressure may act prevents prior art devices from functioning optimally while the patient is in the prone or supine position. Furthermore, the placement of the reservoir in prior art devices increases the working distance between the source of negative pressure and the internal wound, necessitating that it act on a larger volume, reducing the efficiency of the device, and creating a source of oscillating pressure in the case of a temporary blockage which is suddenly freed. Third, prior art devices make use of a perforated internal drain which allows the collection of fluid. The present system comprises a manifold which allows the use of the unique internal drain described herein or the use of one or more of the many conventional internal drainage structures which the surgeon may prefer. Further, the present invention incorporates adaptor fittings which allow any size or sizes (in the case of multiple drain lines) to be utilized.

Additionally, prior art devices prescribe the application of a pressure regime from 125 mmHg to 200 mmHg below atmospheric. At this range, it is unlikely that the device will impart sufficient force on any impediment to flow which may become lodged in the drainage tubing such as a mass of clotted blood, fibrous material, or small portion of tissue. The present invention may operate at a pressure above 200 mmHg for certain periods of operation, such as the initial drawing together of the separated (surgically or otherwise) tissue and the clearing of a blockage. At other times, the present invention may operate at lower pressures in order to allow a more passive means of suctioning. Further, prior art devices do not incorporate a disposable reservoir, and do not allow neutralizing any odor from the collected fluid. The present invention comprises a fluid reservoir inherently designed to be disposable, and is placed downstream from the source of negative pressure, negating the previously described problems with prior art devices.

Prior art devices do not allow for the accurate measurement of collection fluid, or derivative measurements. The present invention allows for the measurement of the amount of collected fluid in either the input manifold or the reservoir, and further calculates the calculation of the percentage of collected fluid to air which would allow for the prediction of poor suturing and possibly surgical site infection (SSI). To accomplish this, the present invention carries out the following steps:
1. Calculating the amount of total volume (air plus liquid) collected via counting revolutions of peristaltic rotor.
2. Calculating the collected fluid amount by positioning a series of electrode pairs acting as graduations in the reservoir or by making use of the fluid measurement units in the manifold.
3. Calculating the ratio of total collected volume to total collected fluid.

In order to provide a context for the various computer-implemented aspects of the invention, the following discussion provides a brief, general description of a suitable computing environment in which the various aspects of the present invention may be implemented. A computing system environment is one example of a suitable computing environment, but is not intended to suggest any limitation as to the scope of use or functionality of the invention. A computing environment may contain any one or combination of components discussed below, and may contain additional components, or some of the illustrated components may be absent. Various embodiments of the invention are operational with numerous general purpose or special purpose computing systems, environments or configurations. Examples of computing systems, environments, or configurations that may be suitable for use with various embodiments of the invention include, but are not limited to, personal computers, laptop computers, computer servers, computer notebooks, hand-held devices, microprocessor-based systems, multiprocessor systems, TV set-top boxes and devices, programmable consumer electronics, cell phones, personal digital assistants (PDAs), tablets, smart phones, touch screen devices, smart TV, internet enabled appliances, internet enabled security systems, internet enabled gaming systems, internet enabled watches; internet enabled cars (or transportation), network PCs, minicomputers, mainframe computers, embedded systems, virtual systems, distributed computing environments, streaming environments, volatile environments, and the like.

Embodiments of the invention may be implemented in the form of computer-executable instructions, such as program code or program modules, being executed by a computer, virtual computer, or computing device. Program code or modules may include programs, objects, components, data elements and structures, routines, subroutines, functions and the like. These are used to perform or implement particular tasks or functions. Embodiments of the invention also may be implemented in distributed computing environments. In such environments, tasks are performed by remote processing devices linked via a communications network or other data transmission medium, and data and program code or modules may be located in both local and remote computer storage media including memory storage devices such as, but not limited to, hard drives, solid state drives (SSD), flash drives, USB drives, optical drives, and internet-based storage (e.g., "cloud" storage).

In one embodiment, a computer system comprises multiple client devices in communication with one or more server devices through or over a network, although in some cases no server device is used. In various embodiments, the network may comprise the Internet, an intranet, Wide Area Network (WAN), or Local Area Network (LAN). It should be noted that many of the methods of the present invention are operable within a single computing device.

A client device may be any type of processor-based platform that is connected to a network and that interacts with one or more application programs. The client devices each comprise a computer-readable medium in the form of volatile and/or nonvolatile memory such as read only memory (ROM) and random access memory (RAM) in communication with a processor. The processor executes computer-executable program instructions stored in memory. Examples of such processors include, but are not limited to, microprocessors, ASICs, and the like.

Client devices may further comprise computer-readable media in communication with the processor, said media storing program code, modules and instructions that, when executed by the processor, cause the processor to execute the program and perform the steps described herein. Computer readable media can be any available media that can be accessed by computer or computing device and includes both volatile and nonvolatile media, and removable and non-removable media. Computer-readable media may further comprise computer storage media and communication media. Computer storage media comprises media for storage of information, such as computer readable instructions, data, data structures, or program code or modules. Examples of computer-readable media include, but are not limited to, any electronic, optical, magnetic, or other storage or transmission device, a floppy disk, hard disk drive, CD-ROM, DVD, magnetic disk, memory chip, ROM, RAM, EEPROM, flash memory or other memory technology, an ASIC, a configured processor, CDROM, DVD or other optical disk storage, magnetic cassettes, magnetic tape, magnetic disk storage or other magnetic storage devices, or any other medium from which a computer processor can read instructions or that can store desired information. Communication media comprises media that may transmit or carry instructions to a computer, including, but not limited to, a router, private or public network, wired network, direct wired connection, wireless network, other wireless media (such as acoustic, RF, infrared, or the like) or other transmission device or channel. This may include computer readable instructions, data structures, program modules or other data in a modulated data signal such as a carrier wave or other transport mechanism. Said transmission may be wired, wireless, or both. Combinations of any of the above should also be included within the scope of computer readable media. The instructions may comprise code from any computer-programming language, including, for example, C, C++, C#, Visual Basic, Java, and the like.

Components of a general purpose client or computing device may further include a system bus that connects various system components, including the memory and processor. A system bus may be any of several types of bus structures, including, but not limited to, a memory bus or memory controller, a peripheral bus, and a local bus using any of a variety of bus architectures. Such architectures include, but are not limited to, Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computing and client devices also may include a basic input/output system (BIOS), which contains the basic routines that help to transfer information between elements within a computer, such as during start-up. BIOS typically is stored in ROM. In contrast, RAM typically contains data or program code or modules that are accessible to or presently being operated on by processor, such as, but not limited to, the operating system, application program, and data.

Client devices also may comprise a variety of other internal or external components, such as a monitor or display, a keyboard, a mouse, a trackball, a pointing device, touch pad, microphone, joystick, satellite dish, scanner, a disk drive, a CD-ROM or DVD drive, or other input or output devices. These and other devices are typically connected to the processor through a user input interface coupled to the system bus, but may be connected by other interface and bus structures, such as a parallel port, serial port, game port or a universal serial bus (USB). A monitor or other type of display device is typically connected to the system bus via a video interface. In addition to the monitor, client devices may also include other peripheral output devices such as speakers and printer, which may be connected through an output peripheral interface.

Client devices may operate on any operating system capable of supporting an application of the type disclosed herein. Client devices also may support a browser or browser-enabled application. Examples of client devices include, but are not limited to, personal computers, laptop computers, personal digital assistants, computer notebooks, hand-held devices, cellular phones, mobile phones, smart phones, pagers, digital tablets, Internet appliances, and other processor-based devices. Users may communicate with each other, and with other systems, networks, and devices, over the network through the respective client devices.

Thus, it should be understood that the embodiments and examples described herein have been chosen and described in order to best illustrate the principles of the invention and its practical applications to thereby enable one of ordinary skill in the art to best utilize the invention in various embodiments and with various modifications as are suited for particular uses contemplated. Even though specific embodiments of this invention have been described, they are not to be taken as exhaustive. There are several variations that will be apparent to those skilled in the art.

What is claimed is:

1. A device for collection of internal fluid from a wound or incision comprising:
   A) a housing comprising:
      i) at least one fluid inlet connector, ii) a fluid chamber comprising at least one pressure sensing element, iii) at least one peristaltic or positive displacement pump unit, iv) a control unit including a circuit control board, and v) at least one outlet port; and B) at least one fluid collector connected to said at least one outlet port for collection of fluid drained from said wound or incision;

wherein said at least one fluid inlet connector is configured to connect to a drainage structure positioned within said wound or incision;

wherein said at least one fluid inlet connector is in fluid communication with said fluid chamber and said fluid chamber is positioned downstream from said at least one fluid inlet connector;

wherein said fluid chamber is in fluid communication with said at least one peristaltic or positive displacement pump unit;

wherein said at least one peristaltic or positive displacement pump unit is in fluid communication with said at least one outlet port of said housing;

wherein said circuit control board of said control unit is configured to monitor the pressure developed by said at least one peristaltic or positive displacement pump unit in order to selectively run or momentarily stop said at least one peristaltic or positive displacement pump unit to regulate the pressure delivered to the wound or incision site by receiving input data from said at least one pressure-sensing element;

wherein said at least one peristaltic or positive displacement pump unit is configured to create a negative pressure to drain said fluid therethrough into said at least one peristaltic or positive displacement pump unit through said at least one fluid inlet connector and to create a positive pressure between said at least one peristaltic or positive displacement pump unit and said at least one fluid collector to transport said fluid from said at least one peristaltic or positive displacement pump unit to said at least one fluid collector through said at least one outlet port; and wherein all electronic components for operation of components ii), iii), and iv) are present within said housing.

2. The device of claim 1, wherein said at least one fluid collector comprises one or more fluid reservoirs.

3. The device of claim 2, wherein said one or more fluid reservoirs are removably attached to said at least one outlet port.

4. The device of claim 3, wherein said one or more fluid reservoirs are disposable and of a collapsible or non-collapsible nature.

5. The device of claim 2, wherein said one or more fluid reservoirs comprise a fluid intake port and an air release port.

6. The device of claim 5, wherein said one or more fluid reservoirs comprise one or more air-permeable but liquid-impermeable membranes.

7. The device of claim 5, wherein said one or more fluid reservoirs are internally segmented or compartmented.

8. The device of claim 5, wherein said one or more fluid reservoirs are rigid or flexible, in whole or in part.

9. The device of claim 5, wherein said fluid intake port comprises a one-way valve.

10. The device of claim 5, further comprising an activated carbon section proximate said air release port.

11. The device of claim 5, further comprising means to measure the amount of fluid in said one or more fluid reservoirs.

12. The device of claim 2, wherein said at least one pump unit is a peristaltic pump with a central rolling mechanism sequentially compressing an internal flexible tubing.

13. The device of claim 1, further comprising a first one-way valve at said at least one fluid inlet connector and a second one-way valve at said at least one outlet port.

14. The device of claim 1, further comprising a binder to which said device is removably attached.

15. The device of claim 1, wherein said pump unit further comprises a wireless communications unit to wirelessly communicate some or all of said input data to an external computing device.

16. The device of claim 1, further comprising one or more sensors adapted to measure biological or chemical properties or parameters, or combinations thereof, of the collected fluid, further wherein said properties or parameters include one or more pH, cytokines, chemokines, reactive oxygen species, or protein levels.

17. The device of claim 1 wherein said device exhibits collection unit-fill detection facilitated by tracking operation of said pump at a known flow rate or displacement per amount time.

* * * * *